(12) United States Patent
Brewer et al.

(10) Patent No.: US 7,020,521 B1
(45) Date of Patent: Mar. 28, 2006

(54) METHODS AND APPARATUS FOR DETECTING AND/OR MONITORING HEART FAILURE

(75) Inventors: James E. Brewer, Lino Lakes, MN (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 195 days.

(21) Appl. No.: 10/291,267

(22) Filed: Nov. 8, 2002

(51) Int. Cl.
*A61N 1/365* (2006.01)

(52) U.S. Cl. .................................................. 607/14

(58) Field of Classification Search ........ 600/515–518; 607/9–14, 44
See application file for complete search history.

(56) References Cited

U.S. PATENT DOCUMENTS

| | | | |
|---|---|---|---|
| 4,960,129 A | 10/1990 | dePaola et al. ............. 128/695 |
| 5,203,326 A | 4/1993 | Collins .................. 128/419 PG |
| 5,251,634 A | 10/1993 | Weinberg .................... 128/642 |
| 5,299,119 A | 3/1994 | Kraf et al. ............. 364/413.06 |
| 5,344,438 A | 9/1994 | Testerman et al. .......... 607/118 |
| 5,404,877 A | 4/1995 | Nolan et al. ................. 128/671 |
| 5,411,031 A | 5/1995 | Yomtov ....................... 128/706 |
| 5,515,848 A | 5/1996 | Corbett, III et al. ........ 128/642 |
| 5,522,854 A | 6/1996 | Ideker et al. ................... 607/6 |
| 5,531,778 A | 7/1996 | Maschino et al. ........... 607/118 |
| 5,542,430 A * | 8/1996 | Farrugia et al. ............. 600/518 |
| 5,658,318 A | 8/1997 | Stroetmann et al. ........... 607/6 |
| 5,682,901 A | 11/1997 | Kamen ........................ 128/706 |
| 5,700,282 A | 12/1997 | Zabara ........................... 607/9 |
| 5,702,429 A | 12/1997 | King ............................ 607/46 |
| 5,775,331 A | 7/1998 | Raymond et al. ........... 128/741 |
| 5,797,840 A | 8/1998 | Akselrod et al. ........... 600/301 |
| 5,824,027 A | 10/1998 | Hoffer et al. ............... 607/118 |
| 5,830,148 A | 11/1998 | Inukai et al. ................ 600/481 |
| 5,916,239 A | 6/1999 | Geddes et al. ................. 607/14 |
| 5,998,458 A | 12/1999 | Bristow ....................... 514/392 |
| 6,051,017 A | 4/2000 | Loeb et al. ..................... 607/1 |
| 6,058,331 A | 5/2000 | King ............................ 607/62 |
| 6,073,048 A | 6/2000 | Kieval et al. ................. 607/17 |
| 6,144,877 A | 11/2000 | DePetrillo ................... 600/515 |
| 6,171,239 B1 | 1/2001 | Humphrey ................... 600/372 |
| 6,175,764 B1 | 1/2001 | Loeb et al. ..................... 607/3 |
| 6,181,965 B1 | 1/2001 | Loeb et al. ..................... 607/3 |
| 6,185,455 B1 | 2/2001 | Loeb et al. ..................... 607/3 |
| 6,214,032 B1 | 4/2001 | Loeb et al. ..................... 607/1 |
| 6,238,423 B1 | 5/2001 | Bardy .......................... 607/40 |
| 6,266,558 B1 | 7/2001 | Gozani et al. .............. 600/547 |

(Continued)

OTHER PUBLICATIONS

Sverrisdottir, Y.B., Ph.D et al., "Sympathetic Neural Burst Amplitude Distribution: A More Specific Indicator of Sympathoexcitation in Human Heart Failure," *CIRCULATION*, vol. 102 (2000), pp 2076-2081.

(Continued)

*Primary Examiner*—George Manuel

(57) ABSTRACT

Methods and apparatuses are provided for assisting with the diagnosis, monitoring, and/or treatment of patients that are suffering from asymptomatic heart failure or may be susceptible to asymptomatic heart failure. The methods and apparatuses can be implemented with implantable devices. In certain implementations, a method is provided which includes sensing muscle sympathetic nerve activity using at least one nerve sensing electrode that is in electrical contact with a patient's efferent muscle-nerve structure, acquiring a muscle sympathetic nerve activity signal from the sensed nerve activity using a nerve activity sensing circuit operatively coupled to the nerve sensing electrode, and analyzing the nerve activity signal for changes in nerve burst activity indicative of the presence and/or severity of asymptomatic heart failure.

35 Claims, 13 Drawing Sheets

U.S. PATENT DOCUMENTS 6,269,351 B1    7/2001    Black ........................... 706/15
6,292,695 B1 *  9/2001    Webster et al. ............... 607/14
6,522,926 B1 *  2/2003    Kieval et al. ................. 607/44

OTHER PUBLICATIONS

Cohn, J.N., M.D. et al., "*Plasma Norepinephrine as a Guide to Prognosis in Patients with Chronic Congestive Heart Failure,*" *N Engl J Med*, vol. 311, No. 13 (1984), pp 819-823.

Hasking, G.J. et al., "*Norepinephrine Spillover to Plasma in Patients with Congestive Heart Failure: Evidence of Increased Overall and Cardiorenal Sympathetic Nervous Activity,*" *CIRCULATION*, vol. 73, No. 4 (1986), pp 615-621.

Thomas, J.A., M.D. et al., "*Plasma Norepinephrine in Congestive Heart Failure,*" *Am J Cardiol*, vol. 41 (Feb. 1978), pp 233-243.

Goldsmith, S.R., M.D. et al., "*Increased Plasma Arginine Vasopressin Levels in Patients With Congestive Heart Failure,*" *J Am Coll Cardiol*, vol. 1, No. 6 (1983), pp 1385-1390.

Burnett, J.S., Jr. et al., "*Atrial Natriuretic Peptide Elevation in Congestive Heart Failure in the Human,*" *Science*, vol. 231 (Mar. 7, 1986), pp 1145-1147.

Cody, R.J., M.D. et al., "*Plasma Endothelin Correlates with the Extent of Pulmonary Hypertension in Patients with Chronic Congestive Heart Failure,*" *CIRCULATION*, vol. 85, No. 2 (Feb. 1992), pp 504-509.

Dzau, V.J., M.D., "*Relation of the Renin-Angiotensin-Aldosterone System to Clinical State in Congestive State in Congestive Heart Failure,*" *CIRCULATION*, vol. 63, No. 3 (1981), pp 645-651.

Levine, T.B., M.D. et al., "*Activity of the Sympathetic Nervous System and Renin-Angiotensin System Assessed by Plasma Hormone Levels and their Relation to Hemodynamic Abnormalities in Congestive Heart Failure,*" *Am J Cardiol*, vol. 49 (May 1982), pp 1659-1666.

Francis, G.S., M.D. et al., "*Comparison of Neuroendocrine Activation in Patients with Left Ventricular Dysfunction With and Without Congestive Heart Failure: A Substudy of the Studies of Left Ventricular Dysfunction (SOLVD),*" *CIRCULATION*, vol. 82, No. 5 (Nov. 1990), pp 1724-1729.

Rector T.S., Ph.D et al., "*Predicting Survival for an Individual with Congestive Heart Failure using the Plasma Norepinephrine Concentration,*" *Am Heart J*, vol. 114, No. 1, Part 1 (Jul. 1987), pp 148-152.

Leimbach W.N., Jr., M.D. et al., "*Direct Evidence from Intraneural Recordings for Increased Central Sympathetic Outflow In Patients with Heart Failure,*" *CIRCULATION*, vol. 73, No. 5 (May 1986), pp 913-919.

Ferguson D.W., M.D. et al., "*Clinical and Hemodynamic Correlates of Sympathetic Nerve Activity in Normal Humans and Patients with Heart Failure: Evidence from Direct Microneurographic Recordings,*" *J Am Coll Cardiol*, Vo. 16, No. 5 (Nov. 1, 1990), pp 1125-1134.

Francis G.S., M.D. et al., "*Sequential Neurohumoral Measurements in Patients with Congestive Heart Failure,*" *Am Heart J*, vol. 116 (Dec. 1988), pp 1464-1468.

Consensus Trial Study Group, "*Effects of Enalapril on Mortality in Severe Congestive Heart Failure: Results from the Cooperative North Scandinavian Enalapril Survival Study (CONSENSUS),*" *N Engl J Med*, vol. 316, No. 23 (Jun. 4, 1987), pp 1429-1435.

The SOLVD Investigators, "*Effect of Enalapril on Survival in Patients with Reduced Left Ventricular Ejection Fractions And Congestive Heart Failure,*" *N Engl J Med*, vol. 325, No. 5 (Aug. 1, 1991), pp 293-302.

Struijk J.J. et al., "*Cuff Electrodes for Long-Term Recording of Natural Sensory Information,*" *IEEE Engineering in Medicine and Biology*, vol. 3 (May-Jun. 1999), 91-98.

* cited by examiner

METHODS AND APPARATUS FOR DETECTING AND/OR MONITORING HEART FAILURE

TECHNICAL FIELD

The present invention generally relates to implantable devices for use in monitoring and/or treating a patient's heart. More particularly, the present invention concerns methods and apparatuses for detecting and/or monitoring heart failure in patients.

BACKGROUND

Heart failure is a clinical problem of increasing importance. Heart failure is best considered a syndrome that results from any number of cardiac conditions in which the cardiovascular system is unable to meet the demands placed upon it.

Others have disclosed a pacemaker that responds to abnormal conditions of a patient's heart by delivering pacing therapy comprising electrical stimulation to the heart and electrical stimulation to nerves or ganglia in the autonomic nervous system.

Others have also disclosed an implantable medical device that prevents arrhythmia by detecting a risk for arrhythmia and stimulating afferent nerves to prevent the arrhythmia. The device monitors sympathetic and parasympathetic nerve activity for the assessment of arrhythmia risk.

Other have disclosed an implantable medical device for detecting imminent cardiac arrhythmia in response to nerve signal activity in the efferent autonomic nerve system, such that activity sensing circuitry emit an output implying arrhythmia based on sensed neural activity.

Others have also disclosed an external method and apparatus for measuring activity of the autonomic nerve system using ECG signals obtained from a patient at rest to quantify a degree of heart failure. The ECG signals are analyzed by measuring the R—R intervals, generating a Poincaré plot using the intervals, and analyzing the plots to determine a level of heart failure.

Others have also disclosed a method of constructing a unique statistical characteristic of a time series data of a measurable activity (such as the autonomic nerve system for diagnosing autonomic neuropathies). The method computes a Hurst exponent for the time series as a unique statistical characteristic.

There are continuing needs for methods and apparatus that can provide early detection of heart failure, for example, in patients with impaired cardiac systolic performance prior to the clinical recognition of such progressing failure.

SUMMARY

The above stated needs and others are met, for example, by a method for use with an implantable device. This exemplary method includes sensing muscle sympathetic nerve activity over a period of time using at least one implantable electrode, and determining a level of heart failure based on the sensed muscle sympathetic nerve activity.

In accordance with other exemplary implementations, an implantable device is provided, which includes, a housing (e.g., a case) having circuitry and logic at least partially arranged within it. The circuitry is configured to sense muscle sympathetic nerve activity over a period of time using at least one implantable electrode. The logic is operatively coupled to the circuitry and configured to determine a level of heart failure based on the sensed muscle sympathetic nerve activity.

In accordance with certain other exemplary implementations of the present invention, a method for detecting heart failure is provided. Here, the method includes sensing muscle sympathetic nerve activity using at least one nerve sensing electrode that is in electrical contact with a patient's efferent muscle-nerve structure, acquiring a muscle sympathetic nerve activity signal from the sensed nerve activity using a nerve activity sensing circuit operatively coupled to the nerve sensing electrode, and analyzing the nerve activity signal for changes in nerve burst activity indicative of heart failure.

In still other exemplary implementations, an apparatus for detecting heart failure in a patient is provided. The apparatus includes at least one nerve activity sensor and logic coupled to it. The nerve activity sensor is operatively configurable to sense muscle sympathetic nerve activity within a patient and output a corresponding sensed nerve activity signal. The logic is operatively configured to receive the muscle sympathetic nerve activity signal from the nerve activity sensor and analyze the nerve activity signal for changes in nerve burst activity that is indicative of heart failure.

BRIEF DESCRIPTION OF THE DRAWINGS

Features and advantages of the described implementations can be more readily understood by reference to the following description taken in conjunction with the accompanying drawings.

DETAILED DESCRIPTION

Exemplary Stimulation Devices

The techniques described below can be implemented in connection with any stimulation device that is configured or configurable to stimulate or shock a patient's heart, and/or monitor a patient's heart.

The examples described below illustrate implantable stimulation devices with three leads having various components, it should be understood that the techniques herein can be applied to devices having zero, one or more leads, and the lead(s) in certain implementations may be unipolar.

Figure 1A:
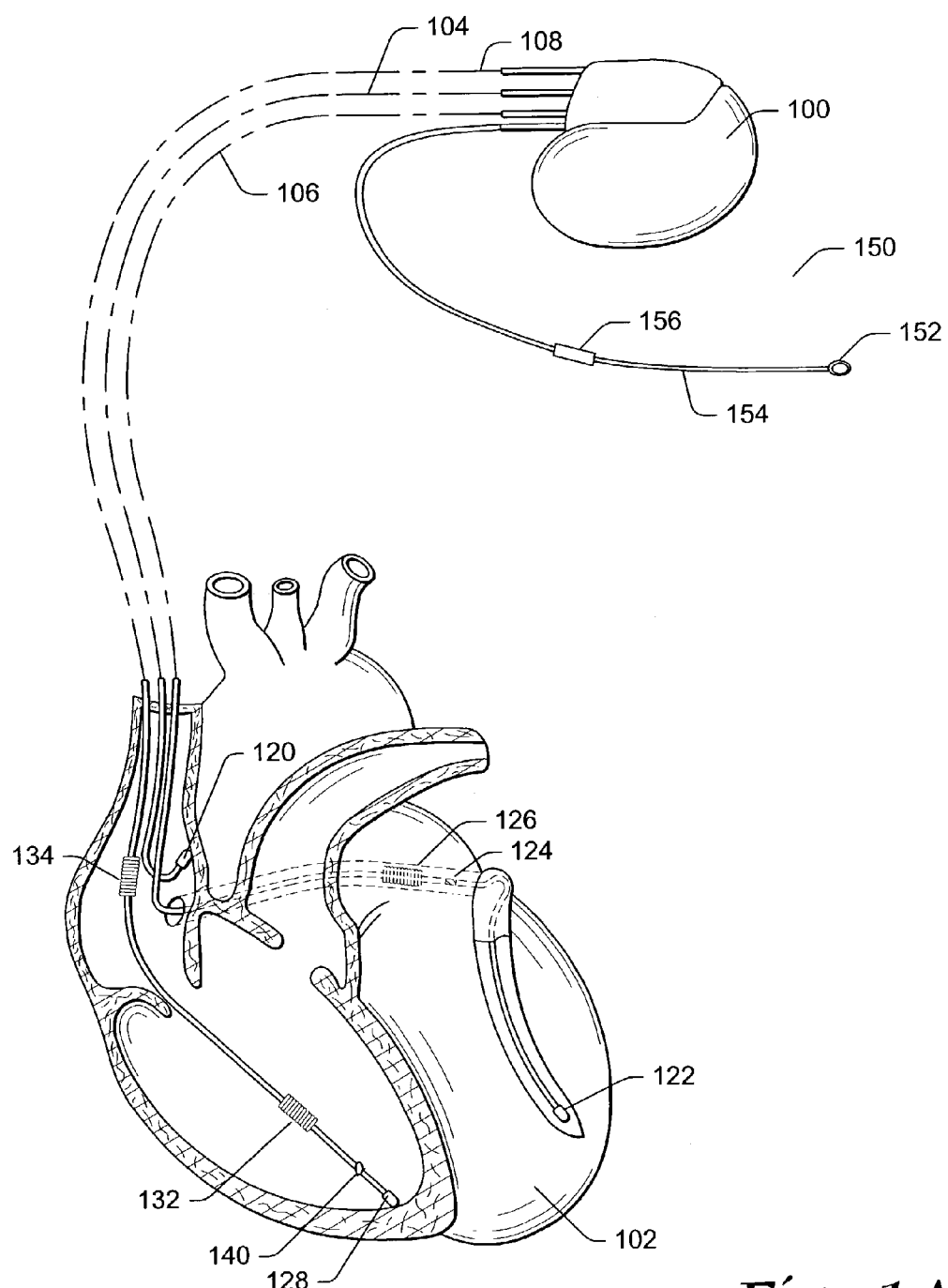
FIGS. 1A, 1B and 1C are simplified diagrams illustrating some implantable stimulation devices that are suitable for detecting and/or monitoring heart failure in patients, in accordance with certain exemplary implementations of the present invention.
Figure 1B:
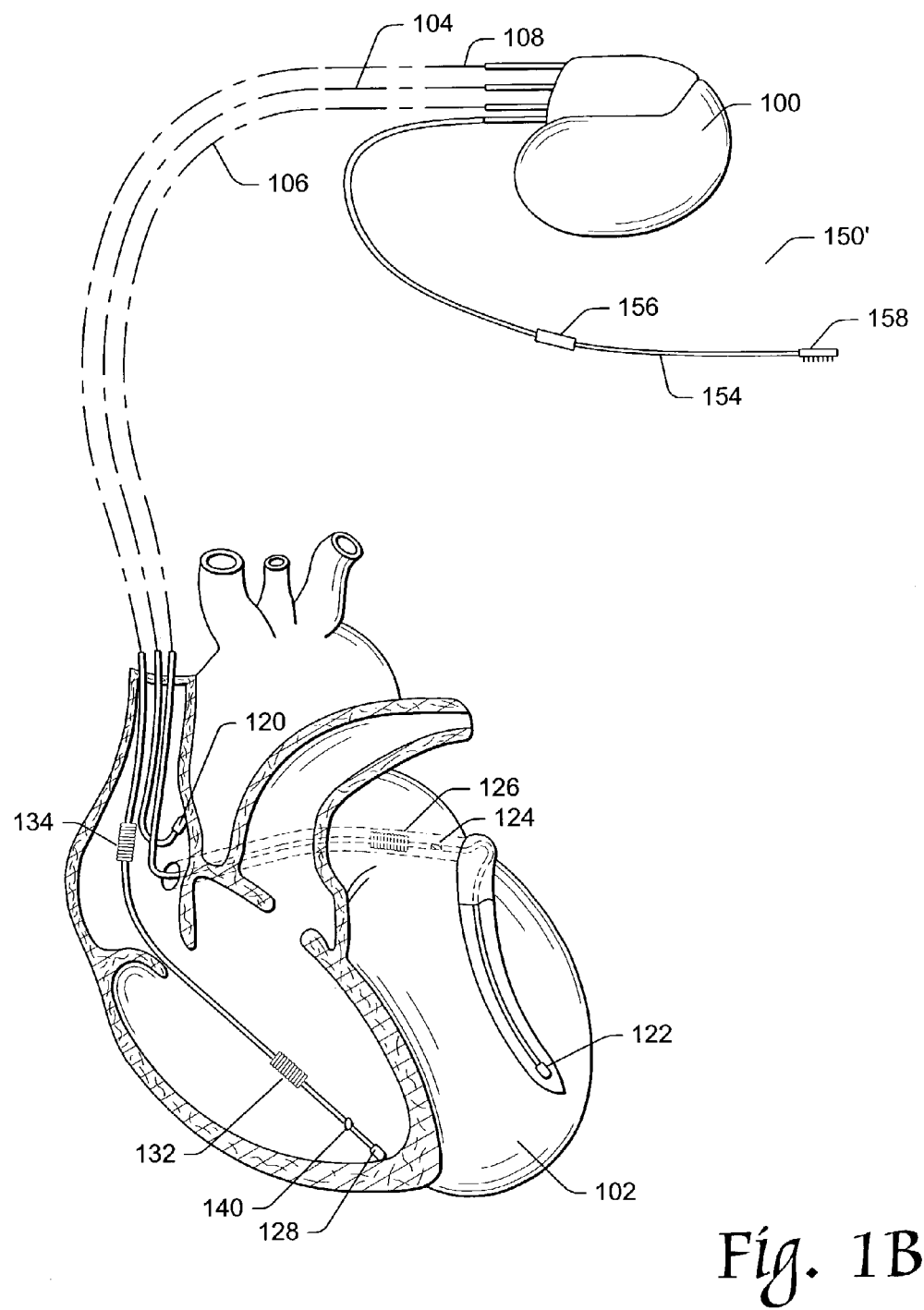
Figure 1C:
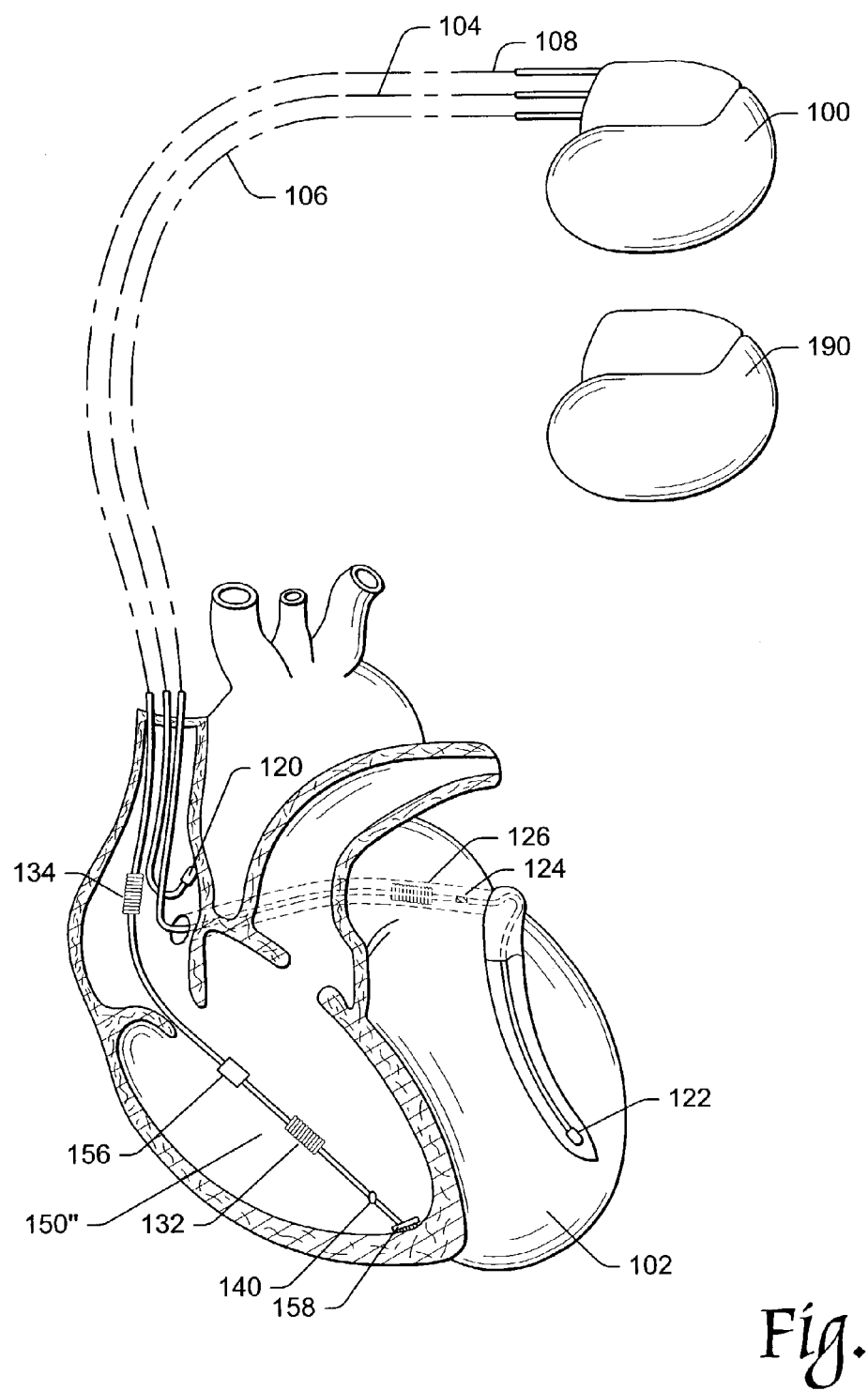

With this in mind, FIGS. 1A–C show exemplary stimulation devices 100 in electrical communication with a patient's heart 102 by way of three leads 104, 106, and 108. These exemplary arrangements are suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the LV and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least an LV tip electrode 122, left atrial pacing therapy using at least a left atrial ring electrode 124, and shocking therapy using at least a left atrial coil electrode 126.

Stimulation device 100 is also shown in electrical communication with the patient's heart 102 by way of an implantable RV lead 108 having, in the implementations in FIGS. 1A–C, a RV ring electrode/sensor 130, an RV coil electrode 132, and an SVC coil electrode 134. The implementations in FIGS. 1A–B also include an RV tip electrode 128, while the implementation in FIG. 1C further includes a reference electrode 156 and a primary monitoring electrode 158. In accordance with still other exemplary implementations, a simulation device 190, e.g., as represented in FIG. 1C, without intra-cardiac leads may be employed and configured to perform certain methods as described herein. These exemplary implementations are described in further detail in subsequent sections.

Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, RV lead 108 is capable of receiving cardiac signals, and delivering stimulation in the form of pacing and shock therapy to the right ventricle.

Figure 3:
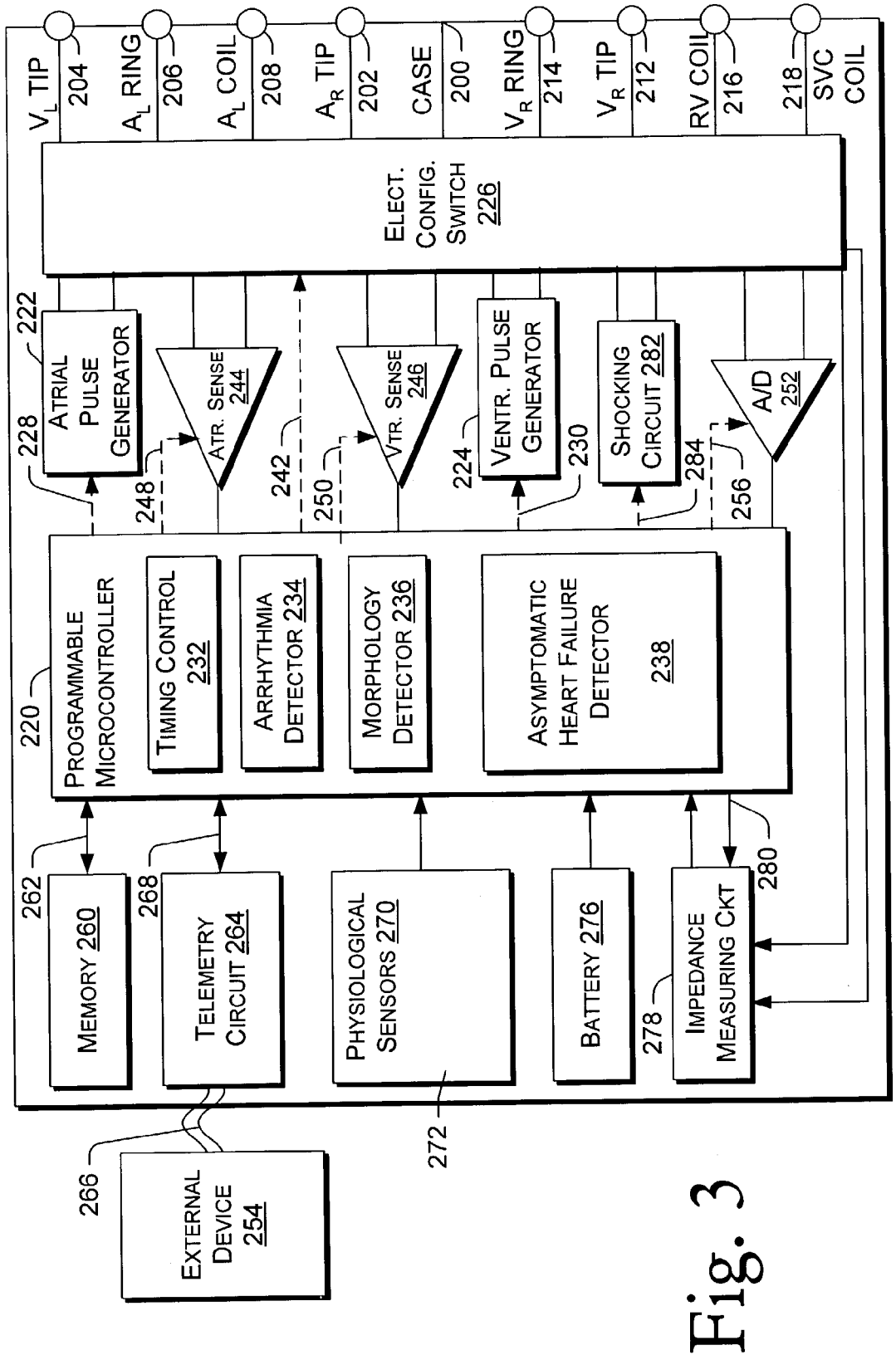
FIG. 3 is a block diagram depicting functional features of an implantable stimulation device, in accordance with certain exemplary implementations of the present invention.

Attention is now drawn to FIG. 3, which depicts an exemplary, simplified block diagram depicting various components of stimulation device 100, e.g., as in FIG. 1.

Stimulation device 100 can be capable of treating both fast and slow arrhythmias with stimulation therapy, including cardioversion, defibrillation, pacing stimulation, monitoring cardiac activity, etc. While multi-chamber devices are shown in FIGS. 1A–C, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

The housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of some exemplary electrodes to which they are connected are shown next to the terminals).

To achieve right atrial sensing and pacing, for example, the connector includes at least a right atrial tip terminal ($A_R$ TIP) 202 adapted for connection to the atrial tip electrode 120. To achieve left chamber sensing, pacing, and shocking, the connector may include a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively, for example. These or other similar terminals may be configured for use with reference electrode 156 and primary monitoring electrode 158.

At the core of stimulation device 100 is a programmable microcontroller 220 that controls the various modes of stimulation therapy and/or cardiac monitoring. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 3 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and a heart failure detector 238. These components can be utilized by stimulation device 100 for determining desirable times to administer various therapies and/or report out certain information, as will become more apparent below. The components 234–238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262, wherein the programmable operating parameters used by the microcontroller 220 are stored and modified, as required, in order to customize the operation of stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

Stimulation device 100 can further include one or more physiologic sensors 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses. While shown as being included within stimulation device 100, it is to be understood that the physiologic sensor 270 may also be external to stimulation device 100, yet still be implanted within or carried by the patient. Examples of physiologic sensors that may be implemented in device 100 include known sensors that, for example, sense respiration rate and/or minute ventilation, pH of blood, ventricular gradient, and so forth. The physiological sensors 270 may further include a pressure sensor that is coupled to detect RV pressure that is sensed by a sensor located at ring 130, which can perform dual functions of a ring electrode and a pressure sensor.

Figure 2:
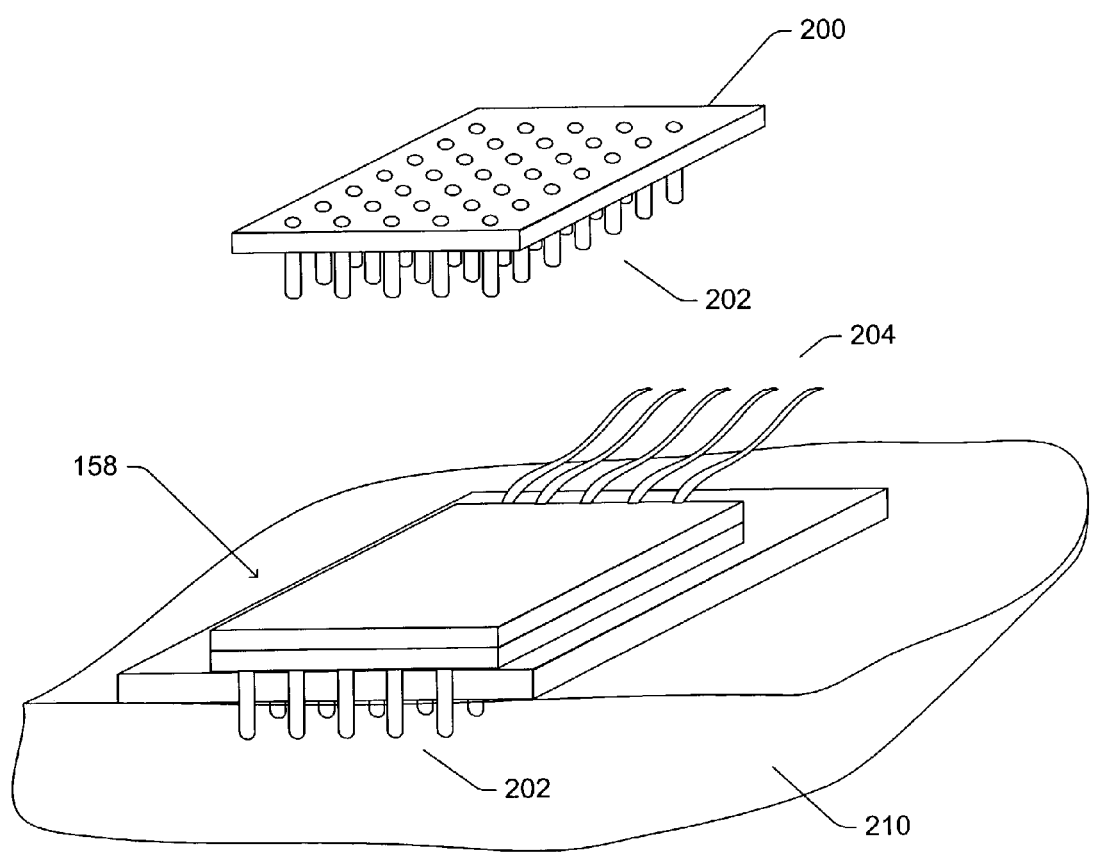
FIG. 2 is an illustrative diagram depicting an electrode-tissue interface, in accordance with certain exemplary implementations of the present invention.

The stimulation device additionally includes a battery 276 that provides operating power to all of the circuits shown in FIG. 2. For stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium/silver vanadium oxide batteries, as is true for most (if not all) current devices.

Stimulation device 100 can further include magnet detection circuitry (not shown), coupled to the microcontroller 220, to detect when a magnet is placed over stimulation device 100. A magnet may be used by a clinician to perform various test functions of stimulation device 100 and/or to signal the microcontroller 220 that the external programmer 254 is in place to receive or transmit data to the microcontroller 220 through the telemetry circuits 264.

Stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (up to 0.5 Joules), moderate (0.5–10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Certain features associated with heart failure detector 238 will now be described in accordance with some exemplary implementations of the present invention.

Detecting Asymptomatic Heart Failure

Heart failure is a clinical problem of increasing importance. Heart failure is best considered a syndrome that results from any number of cardiac conditions in which the cardiovascular system is unable to meet the demands placed upon it. Heart failure is accompanied by important disturbances of the autonomic nervous system. In general, the dysautonomia of heart failure is characterized by increased activity of the sympathetic nervous system and decreased activity of the parasympathetic nervous system.

As is known, patients with heart failure demonstrate elevated resting levels of norepinephrine, vasopressin, atrial natriuretic factor, endothelin, and increased activity of the rennin-angiotensin-aldosterone system. Recently, it has been found that neuroendocrine activation actually precedes the onset of clinically recognized heart failure and that the prognosis of patients with heart failure appears to be inversely related to the magnitude of the neurohormonal excitation.

Microneurography includes techniques that are traditionally used for intraneural study of peripheral nerves. Such techniques may further be extended to the study of sympathetic nerve activity, for example, in deep muscle tissue. This extension permits human neurophysiologic studies of muscle sympathetic nerve activity. Muscle sympathetic nerve activity is regulated by afferent sensory input arising from baroreflex, chemoreflex, and muscle metaboreflex mechanisms. In comparison, skin sympathetic nerve activity is regulated by thermal, respiratory, and emotional stimuli. Skin sympathetic nerve activity has no appreciable influence from baroreceptors or muscle afferents.

Enhanced microneurographic techniques permit the direct assessment of efferent sympathetic nerve activity that is not influenced by peripheral uptake, release, or metabolism of norepinephrine.

Using the enhanced microneurographic techniques for the direct measurement of sympathetic nerve activity, studies have documented that patients with heart failure have resting levels of efferent sympathetic nerve activity to muscle that are significantly greater than the levels of normal resting human subjects. Additional studies have documented that patients with moderate to severe heart failure were observed to have resting levels of muscle sympathetic nerve activity averaging between about 50 and about 60 bursts per minute compared to normal subjects having resting levels averaging between about 15 and about 19 bursts per minute.

More importantly, patients with increasing severity of heart failure demonstrate increasing levels of resting muscle sympathetic nerve activity. The magnitude of increase in this efferent sympathetic neural outflow to muscle tends to parallel the impairment of cardiac performance in these patients.

Certain studies confirm that the level of resting sympathetic nerve activity correlates directly with plasma norepinephrine levels in patients with heart failure.

Therefore, while the precise mechanisms responsible for the inverse relationship between the magnitude of neurohormonal activation characterizing clinical heart failure and survival of this disorder are not yet fully understood, experimental and clinical data now clearly demonstrate that the neuroendocrine excitation is a progressive phenomenon.

The etiology of the neuroendocrine activation in heart failure appears to be related to a significant degree to the loss of normal inhibitory modulating influences of afferent mechanisms arising from cardiopulmonary and arterial baroreceptors. Pharmacological antagonism of the neuroendocrine activation has been shown to improve survival in patients with heart failure, at least with respect to administration of angiotensin-converting enzyme (ACE) inhibitors. More recently, and useful given the present invention, data suggest that these agents may also delay the onset of heart failure in asymptomatic patients with impaired cardiac systolic performance.

The methods and apparatuses of the present invention provide for the early detection of asymptomatic heart failure, for example, in patients with impaired cardiac systolic performance prior to the clinical recognition of such progressing failure.

Here, for example, a patient with a likely impaired cardiac systolic performance is a patient who has recently survived a myocardial infarction or has recently been diagnosed with some form of cardiomyopathy. Such patients are often treated with an ICD as part of the therapy protocol.

In accordance with certain aspects of the present invention, the methods are implemented as a feature provided by the patient's ICD. The methods cause the ICD to monitor the patient for early (e.g., pre-clinical) signs of heart failure. The methods may then cause the ICD to alert the patient and/or his or her physician to the early warning signs detected, thereby permitting the attending physician to aggressively treat the asymptomatic patient with pharmacological antagonists (e.g., ACE inhibitors, digitalis glycosides, or the like) to delay or possibly halt its onset.

With this in mind, an exemplary Asymptomatic Heart Failure Detector (AHFD) apparatus and corresponding method are provided to monitor a patient with a diagnosed cardiac dysfunction for the developing characteristics (e.g., early signs) of heart failure. A diagnosed cardiac dysfunction includes, but is not limited to, right or left atrial dysfunction (atrial flutter, atrial fibrillation), right or left ventricular dysfunction (myocardial infarction and subsequent ventricular wall motion abnormalities, the general class of cardiomyopathies), diabetes, hypertension, etc. The AHFD method and apparatus may be configured to operate as a stand-alone implantable medical device (IMD) (e.g., device 190 in FIG. 1C), or may be embedded in a pacemaker, an ICD platform, or the like.

The exemplary AHFD can be configured to continuously monitor a patient's level of muscle sympathetic nerve activity (MSNA) as a direct measure of neurohormonal activation in the patient. Here, for example, the AHFD may use one or more monitoring sites. In certain implementations, the monitoring sites may take the form of one or more chronic (e.g., cuff or microneurographic) electrodes that are embedded within a patent's patient's muscle, such as, for example, a pectoral muscle comprising a part of an ICD implant pocket.

The exemplary AHFD is configured to acquire and analyze the MSNA signals to construct information and indices regarding a patient's state of progressive heart failure and/or determine that a progression towards heart failure has begun. The analysis and information may be stored locally within the IMD and/or telemetered or otherwise communicated to an external device for storage, display, review, and response by a physician or an automated physician assistant apparatus. In this manner, the AHFD provides significant data and analysis regarding a patient's MSNA, thereby permitting an early detection of asymptomatic heart failure, if such a condition does develop.

Further, an exemplary AHFD may employ the MSNA information and analysis to determine a type and level of therapy to apply to a patient such that the applied therapy changes a patient's presently determined MSNA state.

One type of therapy may be to stimulate one or more nerve sites (and may be different from the monitoring sites) in a manner that indirectly reduces the patient's MSNA. Another type of therapy may be to manage a pharmacological treatment, by providing data and information on the nature of the progression toward or away from heart failure through the analysis of the changes in the MSNA by a drug treatment course.

In certain exemplary implementations, the AHFD monitors the MSNA of a patient either continuously or for periods of time according to a programmable schedule. An index of muscle sympathetic nerve activity (an MSNA index) is computed continuously or is computed periodically at periodic, scheduled/calculated points in time. Here, for example, an MSNA index may indicate the level of nerve activity at any one period of the monitoring process. The AHFD can track the MSNA index as a distribution (e.g., implemented as a histogram, etc.) to determine significant changes in the index over time.

In certain implementations, an AHFD employs a (trained and programmable) neural net that is configured to evaluate the MSNA index histogram for progression towards or away from a possible heart failure condition. Thus, for example, an AHFD may have a plurality of MSNA index thresholds that quantify the level of MSNA and therefore quantify levels of progression towards heart failure. The progression index thresholds define levels of severity such as none, mild, medium, and severe. Using the set of MSNA index thresholds, the AHFD can analyze the information contained in the MSNA index histogram to determine the present level of MSNA and to quantify its significance. A series of increasing serious alarms may then be triggered as an MSNA index histogram progresses through the (programmable) set of MSNA thresholds, as indicated by a significantly increasing level of a patient's MSNA.

An exemplary AHFD can be illustrated by a description of its neurocardiac components and actions, with components including at least one nerve sensing electrode placed in electrical contact with a preselected nerve fiber bundle within a patient's nervous system, a nerve activity sensing circuitry electrically connected to the (at least one) nerve sensing electrode for sensing nerve activity, and diagnostic logic connected to the nerve activity sensing circuitry such that the diagnostic system is responsive to the sensed nerve activity signal from the nerve fiber bundle and analyzes the nerve activity signal to compute therapy decision parameters. The resulting AHFD monitors a patient to detect changes in muscle sympathetic nerve activity sensed at the nerve that indicate a progression toward heart failure in a time period prior to a development of clinical heart failure symptoms; thereby halting or regressing the progressing neurocardiac conditions that lead to heart failure.

A more integrated and comprehensive embodiment of the AHFD may also include a therapy subsystem, such that the general advantages and novel features of the AHFD are illustrated by a description of its integrated, implanted, neurocardiac components and actions, with components that include, for example, at least one nerve sensing electrode placed in electrical contact with a first preselected nerve fiber bundle within a patients nervous system, at least one nerve stimulating electrode placed in electrical contact with a second preselected nerve fiber bundle within a patient's nervous system, nerve activity sensing circuitry electrically connected to the nerve sensing electrode(s) for sensing nerve activity and signal generating circuitry electrically connected to the nerve stimulating electrode(s) for generating and delivering electrical current (e.g., pulses) to the nerve fiber.

Associated diagnostic logic connected to the nerve activity sensing circuitry and to the signal generating circuitry is responsive to the sensed nerve activity signal from the nerve fiber bundle(s) and configured to analyze the nerve activity signal and compute therapy decision parameters. The logic may also initiate appropriate electrical therapy.

The AHFD may act, therefore, to monitor a patient and detect changes in muscle sympathetic nerve activity sensed at the first nerve that indicates a progression toward heart failure in a time period prior to a development of clinical heart failure symptoms. By applying a pulse or other like therapy to a second nerve, the AHFD may act to reverse the detected muscle sympathetic nerve activity changes, such that the AHFD operates as a negative feedback loop to control chronically increasing muscle sympathetic nerve activity to thereby slow down, halt or regress the progressing neurocardiac conditions that lead to heart failure.

Thus, as further illustrated in FIG. 1A, an ICD platform and lead system as previously described can be placed into the heart as needed and at least one MSNA monitoring lead 150 configured to sense nerve activity. Here, for example, the MSNA monitoring lead includes a cuff or cuff-like microelectrode 152 connected to a lead 154. A low-impedance reference electrode 156 is also operatively arranged on lead 154 at a predetermined distance from the primary monitoring electrode 152.

As further illustrated in FIG. 1B, an MSNA monitoring lead 150' is provided. MSNA monitoring lead 150' includes a neurographic-style (e.g., tungsten) microelectrode 158 connected to lead 154 along with a low-impedance reference electrode 156 at a predetermined distance apart from electrode 158.

An exemplary neurographic-style microelectrode 158 is illustratively depicted as being implanted in a patient in FIG. 2. Here, micro electrode 158 includes a base 200 having a plurality of prongs 202 that are connected to a plurality of lead conductors 204. When implanted, prongs 202 are in electrical contact with tissue 210, for example, as depicted in FIG. 2.

The exemplary implementation in FIG. 1C illustrates that an ICD and leads may be configured such that an MSNA monitoring lead 150" is part of a right ventricular (RV) pacing and/or defibrillation lead system. Here, monitoring lead 150" includes a neurographic-style microelectrode 158 placed at the tip of the pacing-defibrillation lead 108, along with and a low-impedance reference electrode 156 a predetermined distance apart.

In other exemplary arrangements, a similar modification to a pacing-defibrillation lead permits the MSNA microelectrode to be placed and to be attached to venous muscle at a point along a lead's venous path to the RV of a patient.

Those skilled in the art will recognize that other arrangements are also possible. Thus, as illustrated in the above examples, an applicable MSNA monitoring lead may be connected to an appropriate location of a patient's neuromuscular structure. In certain implementations, the MSNA monitoring lead may contact a portion of a pectoral muscle forming the ICD implant pocket. An appropriate location is any suitably accessible muscle fascicle (bundle) that is associated with efferent postganglionic sympathetic neural activity.

There are various methods and apparatus for constructing and implanting cuff and microneurographic electrodes. The present state-of-the-art neural electrode systems are exemplified by the apparatus specified in U.S. Pat. Nos. 5,251,634; 5,344,438; 5,515,848; 5,531,778; and, 5,824,027. As an illustration, the specification of U.S. Pat. No. 5,344,438 discloses a cuff electrode suitable for the purposes of the requirements for cuff-like microelectrode 152. As a further illustration, the specification of U.S. Pat. No. 5,515,848 discloses an electrode suitable for the purposes of the requirements for neurographic-style microelectrode 158.

There are important design considerations that are understood and that are incorporated into the design and operation of a cuff electrode for the present invention. Preferably, MSNA monitoring lead 150 can be part of a long-term implant with minimal tissue and nerve damage.

U.S. Pat. No. 5,775,331 describes a method and apparatus for locating a nerve, and is therefore incorporated herein by reference in its entirety.

In the block diagram of FIG. 3, AHFD 238 is provided and operatively arranged along with other logic and the plurality of physiologic sensors to measure and collect diagnostic data. Additionally, a plurality of treatment delivery hardware for pacing and defibrillation therapies is also provided that can be directed/used by AHFD system 238.

Further, an alternative implementation includes the stand-alone IMD 190 in FIG. 1C. Such a design permits the construction and deployment of an extremely small and inexpensive device because the device is required to only monitor MSNA. There are no pacing or defibrillation energy requirements. Further to this preferred embodiment, the AHFD IMD does not require any leads or lead system. Here, the AHFD case (200) itself serves as the system's microneurograph, with electrode components as part of the housing's exterior, and with the housing design as inner and outer compartments. In certain implementations a stand-alone AHFD case could be fairly small so as to be easily placed subcutaneously in a patient's limb, etc. The stand-alone AHFD case would monitor a patient and telemeter or otherwise communicate to another device the monitoring results according to a periodic schedule, etc. In this manner, many different patient needs are met without requiring a patient to fall into a category of significant ventricular impairment.

Figure 4:
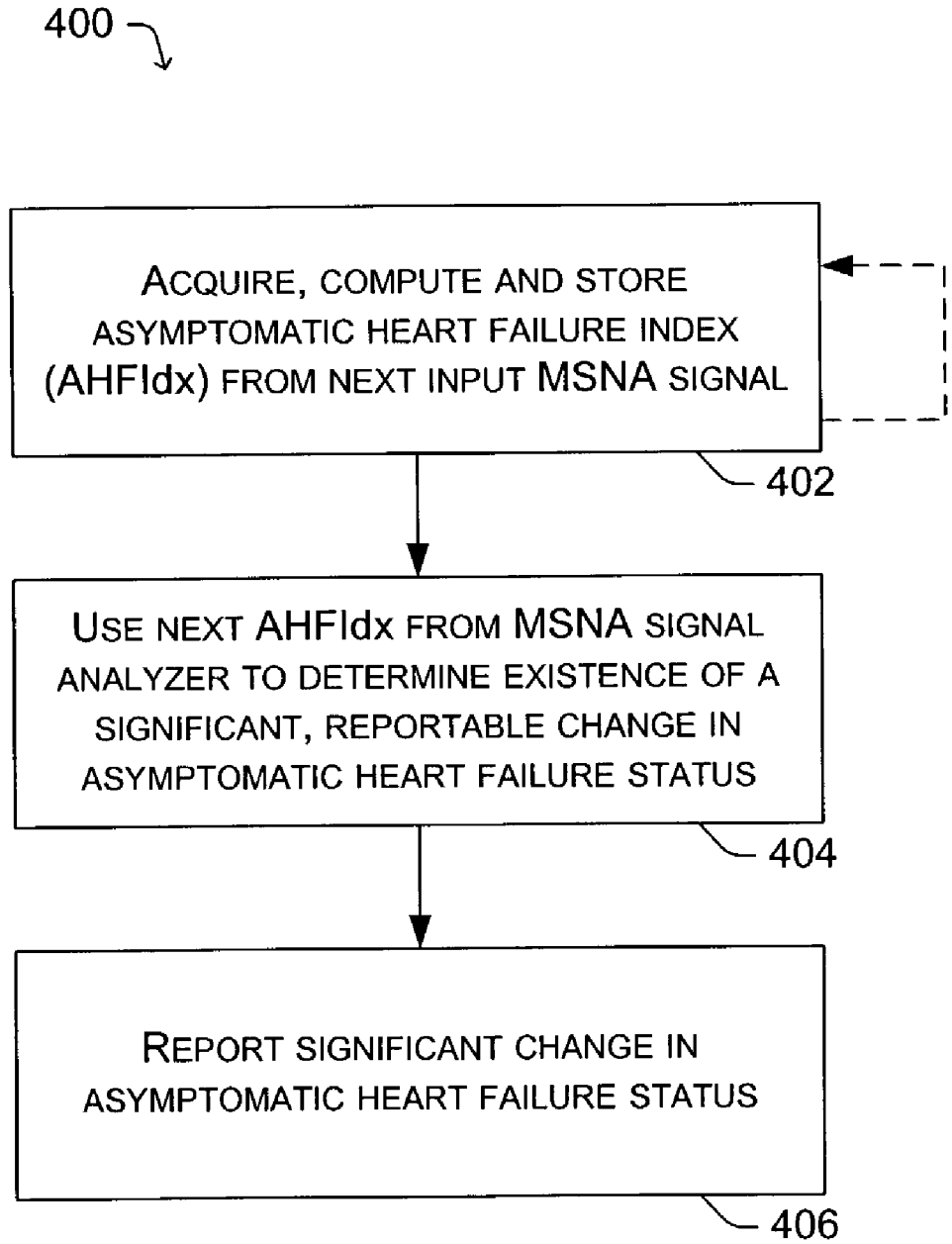
FIG. 4 is a flow-diagram depicting a method for determining heart failure, in accordance with certain exemplary implementations of the present invention.

Attention is now drawn to FIG. 4, which depicts a flow diagram illustrating an AHFD method 400, in accordance with certain exemplary implementations of the present invention. Method 400 includes an MSNA signal acquisition and analysis act 402, in which the AHFD collects a digital representation of an MSNA signal using at least one electrode, and analyzes the MSNA signal either continuously or periodically at regularly scheduled, preferably programmable, points in time and stores an asymptomatic heart failure index (AHFIdx). Act 402 can run in series or in parallel with other operational tasks of the AHFD or other ICD system.

For example, in certain implementations, act 402 is performed continuously, segmenting the signal into x-number of beat sections (e.g., 100 beat sections). This acquisition and analysis act then processes the MSNA segment to compute an Asymptomatic Heart Failure Index (AHFIdx) for the MSNA signal segment. The processing of a MSNA signal segment and the computation of the AHFIdx can also be performed in parallel to the acquisition of the next MSNA signal segment. The tasks required to process a MSNA signal can be performed in parallel, so that an AHFIdx is computed for its associated MSNA signal segment prior to the completion of acquiring the next MSNA signal segment. In this manner, a new AHFIdx is computed for a patient every x-number of beats.

Acquisition and analysis act 402 provides the computed AHFIdx to an Asymptomatic Heart Failure Status (AHFS) act 404. AHFS act 404 uses a newly provided AHFIdx in its next determination of whether a significant change in the heart failure status of a patient has occurred. The AHFS block 404 uses a sequence of contiguously computed AHFIdx values, of a predetermined number, stored in a ring buffer structure, to compute a new value for a patient's asymptomatic heart failure status. Thus, in certain implementations, AHFS act 404 computes a new heart failure status value for each new AHFIdx from acquisition and analysis act 402.

The output from AHFS act 404 is a patient heart failure status record that may include, for example, a digitized MSNA signal segment, the corresponding gained and doubly filtered MSNA data stream, an associated AHFIdx data ring buffer with the newly computed AHFIdx value as the last value, and an associated AHFS value. This or other like record is then provided to an asymptomatic heart failure reporting act 406 for communication to an external device for storage and further analysis and review, e.g., by a patients physician or authorized personnel.

Asymptomatic heart failure reporting act 406 in certain implementations issues alarms of increasing severity that match the value of the determined heart failure status. Asymptomatic heart failure reporting act 406 may, for example, be programmed to issue an audible or tactile alarm to the patient, and/or a receiving storage and review station can respond by issuing alarms to the physician in various forms, such as, for example, audible alarms, visual alarms, and electronic alarm reports within a physician's medical records system and network. In this manner, the AHFD operates to continuously monitor a patient for changes in muscle sympathetic nerve activity that indicate an early and significant warning of the onset, progression, and/or regression of asymptomatic, pre-clinical heart failure.

Figure 5:
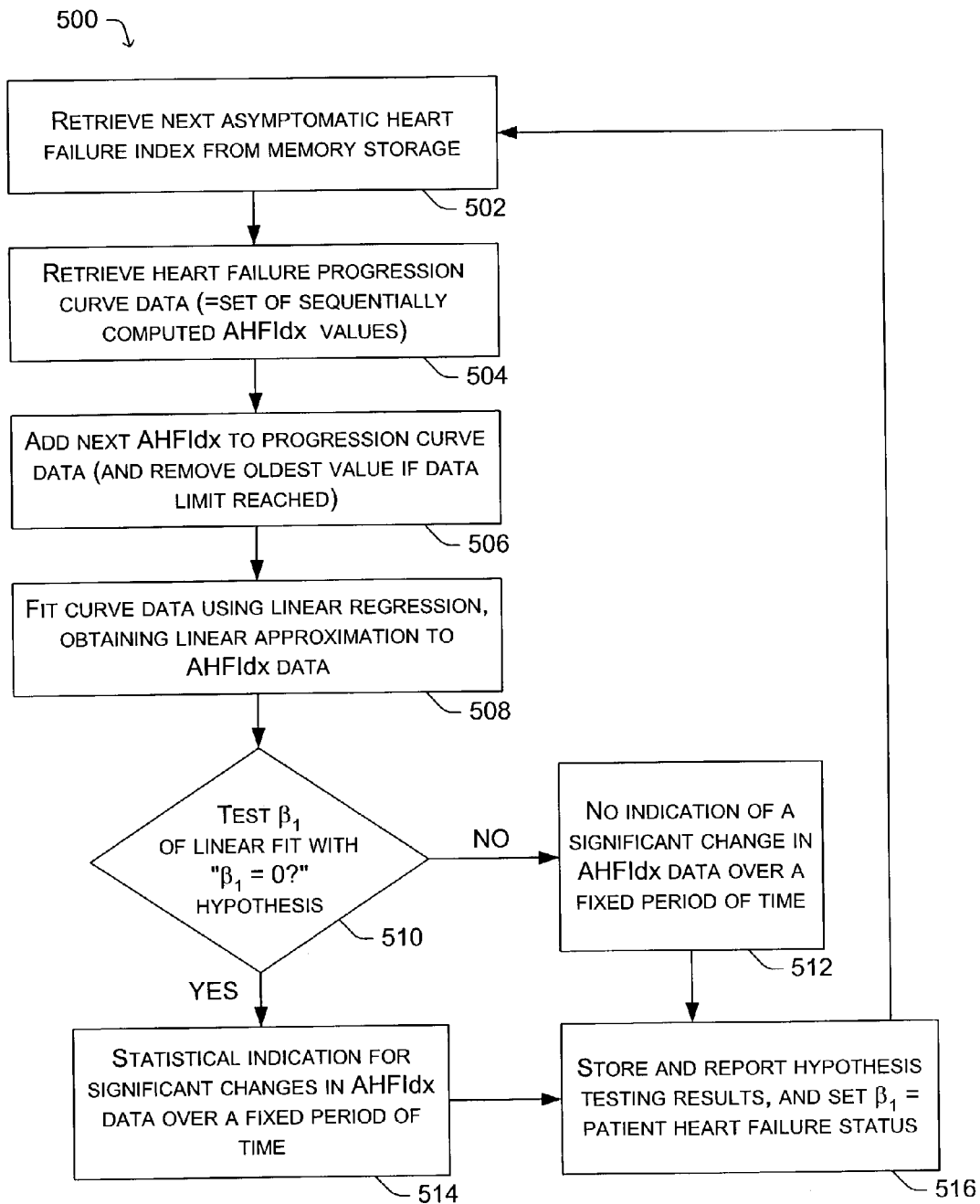
FIG. 5 is a flow-diagram depicting a method for use in determining heart failure, in accordance with certain further exemplary implementations of the present invention.

FIG. 5 illustrates the details to the operation of the Asymptomatic Heart Failure Status (AHFS) act 404, now labeled AHFS method 500. In act 502, a next asymptomatic heart failure index (AHFIdx) is retrieved from a memory location. The AHFIdx was stored by the acquisition and analysis act 402, which can be configured to signal act 502 that a newly computed AHFIdx resides in the AHFIdx value storage location. A time stamp for the AHFIdx value may also be provided in the resulting stored AHFIdx value record.

In act 504, a heart failure progression data set (e.g., curve data) is retrieved, for example from a ring buffer or other like data storage configuration. In act 506, the retrieved AHFIdx value from act 502 is included in the data set. If the data set is stored in a ring buffer data arrangement, then the oldest residing AHFIdx value would be removed from the data set. In this manner, AHFS method 500 maintains an updated set of AHFIdx values for a predetermined period of time. The number of AHFIdx values maintained in a ring buffer data arrangement can be determined, for example, based one the desired robustness and sensitivity of the overall heart failure detector operation. If a small number of AHFIdx values are maintained (for example in the range of about 10 to about 100), then the detection process reacts to changes that occur over a short period of time and is more sensitive and less robust to noise and to short term changes in MSNA. For example, in certain exemplary implementations, 10 AHFIdx values represents approximately 12.5 to 16.7 minutes of time, and 100 AHFIdx values represent approximately 2.1 to 2.7 hours of time, assuming a range of about 60 to about 80 heart beats per minute.

Conversely, a larger number of AHFIdx values provides more robust analysis and monitoring, and is not as sensitive to small or abrupt changes to the MSNA due to daily patient activities. For example, about 10,000 AHFIdx values represents approximately 8.9 to 11.6 days of time. An amount of time approximately 1 to 2 weeks in length for the long-term detection of heart failure appears to provide a sufficiently robust resilience to hourly or daily autonomic noise without the likelihood of missing the important, gradual changes that occur to the MSNA prior to onset of heart failure or its increase in severity. However, 10,000 AHFIdx values require approximately 10 K bytes of storage and require a significant amount of processing time for each newly computed AHFIdx. Methods are well-known in the digital signal processing community to design the AHFD to operate using about 10,000 AHFIdx values as an aggregated, sized-down, ring buffer without the loss of any information and to also provide significant increases in computation speed.

In other exemplary implementations, the length of the MSNA segments can be increased from about 100 beat lengths to about 700 beat lengths, thereby permitting about a 1–2 week window for the heart failure detector analysis and requiring significantly fewer AHFIdx values.

In still other exemplary implementations, the MSNA segments can be processed in series in a manner that computes a new AHFIdx after longer periods of time, thereby requiring significantly less AHFIdx values. The AHFD may also be programmed to skip a predetermined number of new AHFIdx values prior to selecting a newly computed AHFIdx for determining the next heart failure status.

Next, in act 508, the AHFIdx data set is used as the y values in a set of (x, y) coordinate pairs, wherein the x value represents the relative amount of time from the oldest AHFIdx value to the newest AHFIdx value. The time values can be updated each time a new AHFIdx value is acquired and the oldest value is removed from the ring buffer data arrangement, for example.

The x coordinates can be constructed using the time stamps attached to each AHFIdx value. In this example, the AHFS method fits (e.g., models) the (relative time, AHFIdx) pairs with a simple linear regression model using the method of least squares to obtain a linear model approximation for the AHFIdx data set.

For example, the model (line fit) may be represented as $Y=\beta+\beta_{S1} X_1$ with $\beta$ representing the y-intercept and $\beta_{S1}$ representing the slope of the fitted line. In act 510, the AHFS method tests $\beta_{S1}$ to determine whether $\beta_{S1}$ is significantly different from 0. $\beta_{S1}$ may be tested, for example, against the hypothesis of no trend in the population by computing the ratio of $\beta_{S1}$ to the standard error of the slope and comparing the ratio with the two-tailed critical value $t_\alpha$, where $\alpha=95$ or $\alpha=99$. In act 514, if $\beta_{S1}$ is significantly different from 0, then there is a statistically significant trend in the level of MSNA and $\beta_{S1}$ further indicates whether the trend is for increasing or decreasing MSNA. Otherwise, in act 512, there is no increasing or decreasing trend for the AHFIdx data over a fixed period of time (e.g., as defined by the length of each MSNA signal segment and the number of AHFIdx values used for the simple linear modeling).

In act 516, the value for $\beta_{S1}$ is redefined as the Asymptomatic Heart Failure Status (AHFS) value, to be used as an indication of decrease, no change, or increase in MSNA over a fixed period of time for a patient. Also in act 516, the AHFS method constructs a patient heart failure status record, e.g., as previously described, and stores the record for transmission by act block 406 (FIG. 4).

Figure 9:
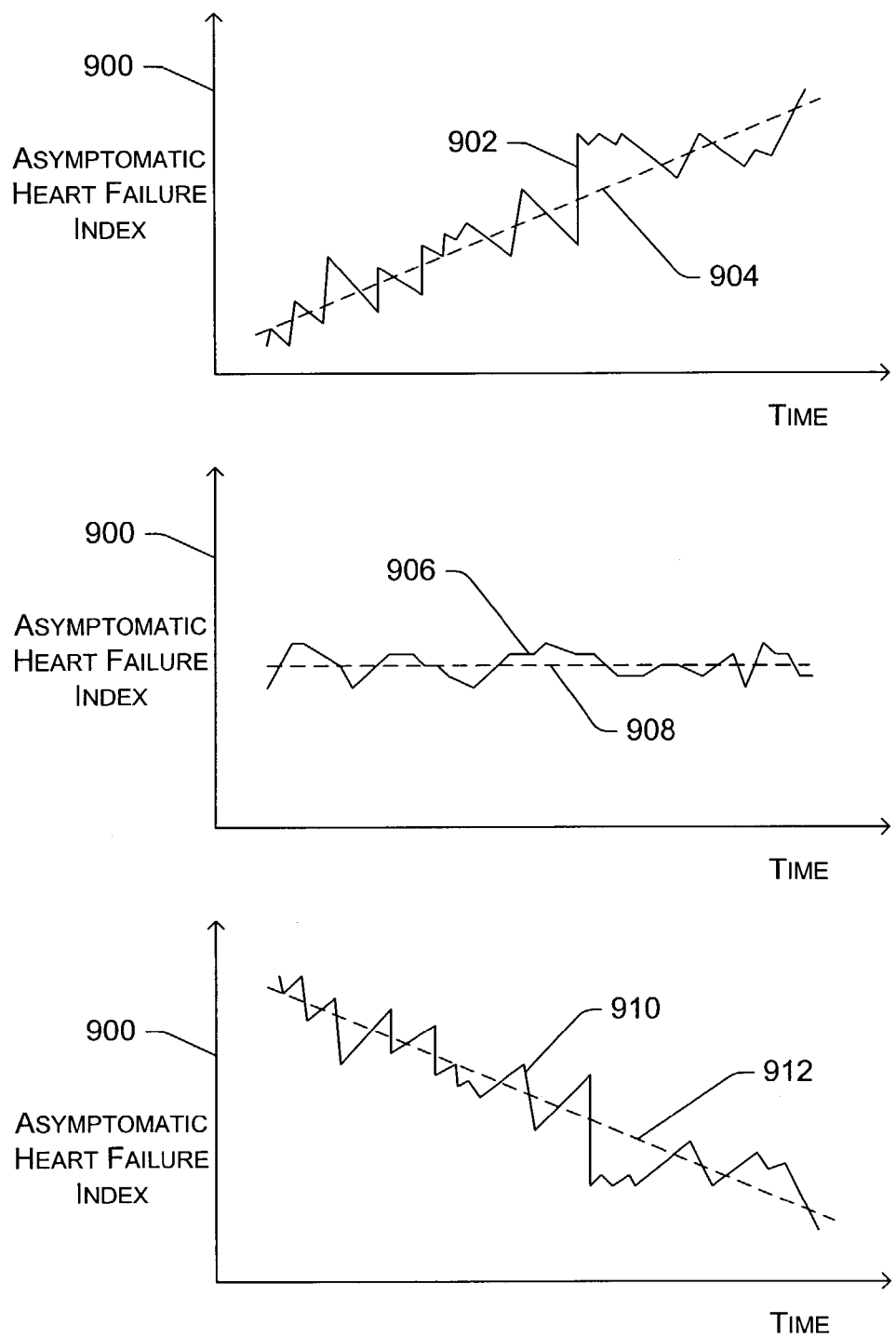
FIG. 9 depicts three graphs showing different detected heart failure index functions, in accordance with certain further exemplary implementations of the present invention.

Reference is now made to FIG. 9, which includes three graphs illustrating scenarios of short term analysis of heart failure indices that characterize changes. As shown, the graphs illustrate how a simple linear model may be employed for a series of asymptomatic heart failure index values, e.g., in a ring buffer arrangement. Each graph 900 plots the set of (x, y) coordinate pairs, where the x values represent the relative amount of time from the oldest AHFIdx value and the newest AHFIdx value, and where the y values are the AHFIdx data set values. The first graph illustrates an increasing data set of AHFIdx 902 and a corresponding simple linear model 904 having a positive slope ($\beta_1>0$). This indicates, based on MSNA signal data that a patient's asymptomatic heart failure condition may be worsening.

The second graph illustrates a data set of AHFIdx 906 with no long term changes, such that a corresponding simple linear model 908 has a zero slope ($\beta_1=0$). This would be indicative that, based on MSNA signal data, a patient's asymptomatic heart failure condition is not significantly changing from a previously known state.

The third graph illustrates a data set of AHFIdx 910 with decreasing values. Here, a corresponding simple linear model 912 has a negative slope ($\beta_{S1}<0$), which is an indication that, based on the MSNA signal data, a patient's asymptomatic heart failure condition is improving.

The simple linear regression modeling technique used in these examples can be constructed using the least-squares regression technique (or $L_2$ regression). There are many other well-known techniques that can also be used to construct an appropriate linear model. A partial list of such techniques are the least-absolute-deviations regression ($L_1$ regression), the Huber M-regression technique, the method of weighted medians (non-parametric), Bayesian regression, and ridge regression. Least-squares regression tends to be significantly optimal if the distribution of the error population is normal. The method of least-absolute-deviations (LAD) regression tends to be more efficient when the error distribution has heavy tails, and is effective a controlling bias. The LAD, M, and nonparametric regression techniques may be appropriate for data containing outliers. Ridge regression may provide more accurate estimates when there are collinearities among the explanatory variables.

Because the exemplary AHFD described above uses a single explanatory variable (AHFIdx as a function of time), the AHFD uses a large number of AHFIdx values, and an AHFIdx: is computed using a significant portion of filtered MSNA signal data, there is a low likelihood of a non-normal error distribution or disruptive outliers in the AHFIdx values.

Nonlinear modeling techniques may also be employed to construct a more accurate nonlinear fit to the data. For example, nonlinear regression techniques extract nonlinear information from the data which may provide additional and significant pertinent information regarding a patient's onset or progression to clinical heart failure. Exemplary nonlinear methods include the method of logistic regression (using techniques such as steepest descent, the Gauss-Newton method, or the Marquardt method to construct the regression model). In particular, in certain implementations, logistic regression may be applied, such that the AHFS value represents the probability that a patient is indeed progressing towards or away from significant different levels of heart failure. Here, for example, the nonlinear characteristic of a progression curve also quantifies the rate of progression.

Furthermore, in certain implementations, a neural network (or neural net) may be employed to construct a more accurate nonlinear fit to the data. The neural net may be dynamically trained, for example, using a predetermined subset of the presently available AHFIdx data set values over time, where, for example, a predetermined subset may be the first (older) half of the AHFIdx data set. The neural net may also use a predetermined subset of the presently available AHFIdx data set values to test for significant changes, where, for example, a predetermined subset may be the second (newer) half of the AHFIdx data set. The neural net can be constructed to output values in the range of [0,1], in a similar manner as the logistic regression model, such that, for example, the output value represents the probability that a patient is progressing towards or away from significant different levels of heart failure.

Other methods of using linear and nonlinear modeling techniques may also be employed to construct an accurate fit to the data, construct information about the data related to detecting significant clinical changes as indicated by the AHFIdx data set, etc. For example, modeling techniques such as discriminant function analysis, MANOVA, MANCOVA, bootstrap analysis, fuzzy set modeling, genetic algorithms, and the like are well-known and may be employed by those skilled in the art.

Figure 6:
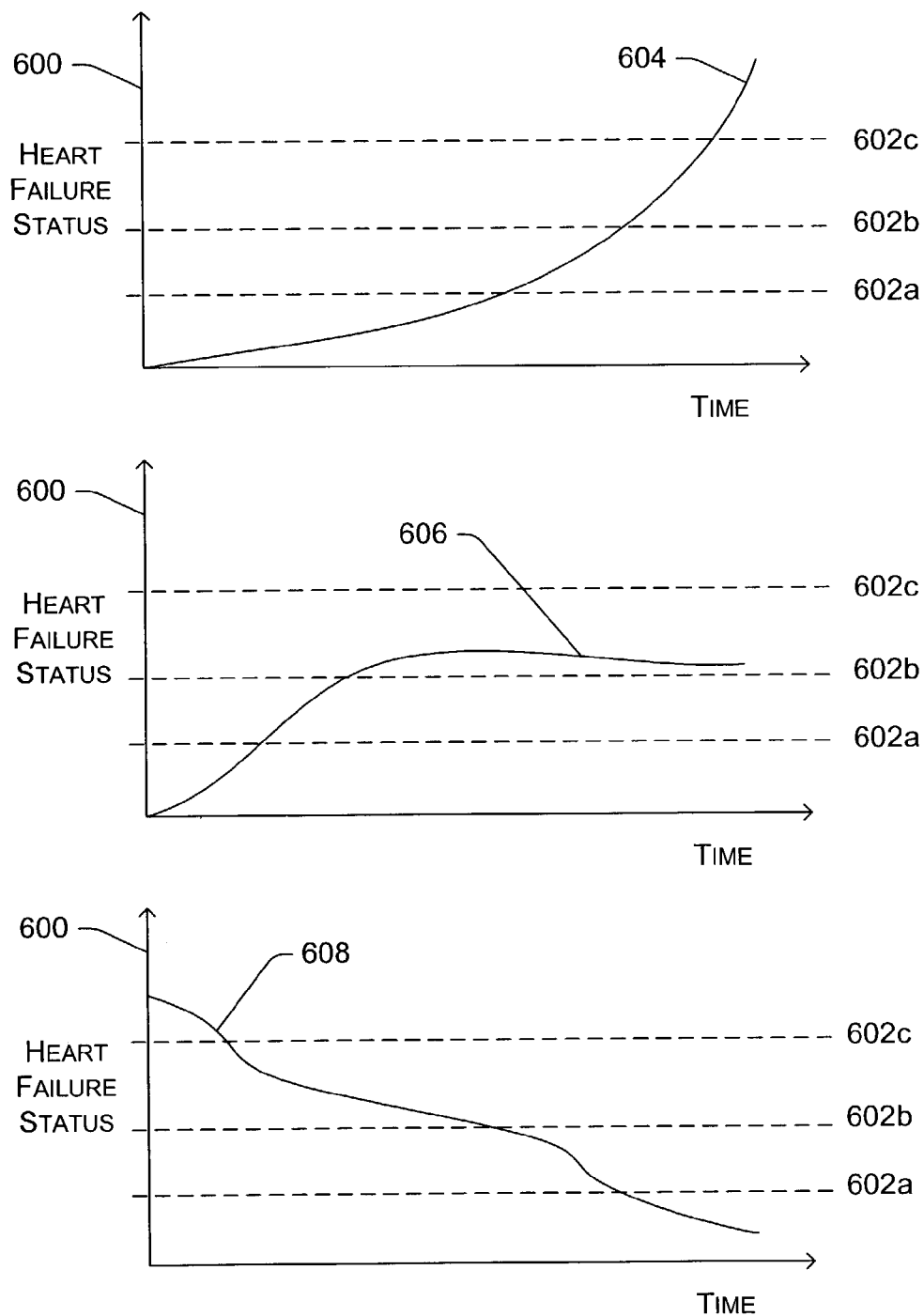
FIG. 6 depicts three graphs showing different detected heart failure conditions, in accordance with certain further exemplary implementations of the present invention.

Attention is now drawn to FIG. 6, which illustrates scenarios for changes in the AHFS values over certain longer periods of time. Here, graphs 600 represent relative or absolute time on the x-axis and heart failure status ($\Box_{51}$) on the y-axis. In the first graph a patient's steadily progressing heart failure status 604 is shown as crossing through increasingly predefined severe levels 602a–c over time. In certain implementations, therefore, AHFS has associated with it a set of severity levels that indicate the significance of the level of progression towards heart failure and progression towards worsening heart failure. For example, a straightforward set of severity levels can be labeled none, mild, medium, and severe. As shown in FIG. 6, a none severity level would be for AHFS less than or equal to 602a, a mild severity level would be for AHFS greater than 602a but less than or equal to 602b), a medium severity level would be for AHFS greater than 602b but less than or equal to 602c, and a severe severity level would be for AHFS greater than 602c.

Consequently, a first alarm can alert a patient or a physician when a patient's AHFS crosses from no significant heart failure to a mild state of heart failure. Additional alarms can alert a patient or a physician as a patient crosses into each of the other severity ranges.

The center graph represents a patient whose progressing heart failure status 606 has been arrested prior to becoming severe and whose condition continues to hold steady (due to treatment, for example) over time. The lower graph represents a patient whose progressing heart failure status 608 has been reversed from severe to a negligible level, as measured by MSNA.

The set of severity levels, such as, e.g., 602a–c, can be continuous, or defined in many different manners, to reflect important aspects of the AHFD, such as the long-term monitoring and measurement of MSNA for early detection of asymptomatic heart failure. Note that the definition of the asymptomatic heart failure status value implies that the MSNA is increasing over time.

Figure 7:
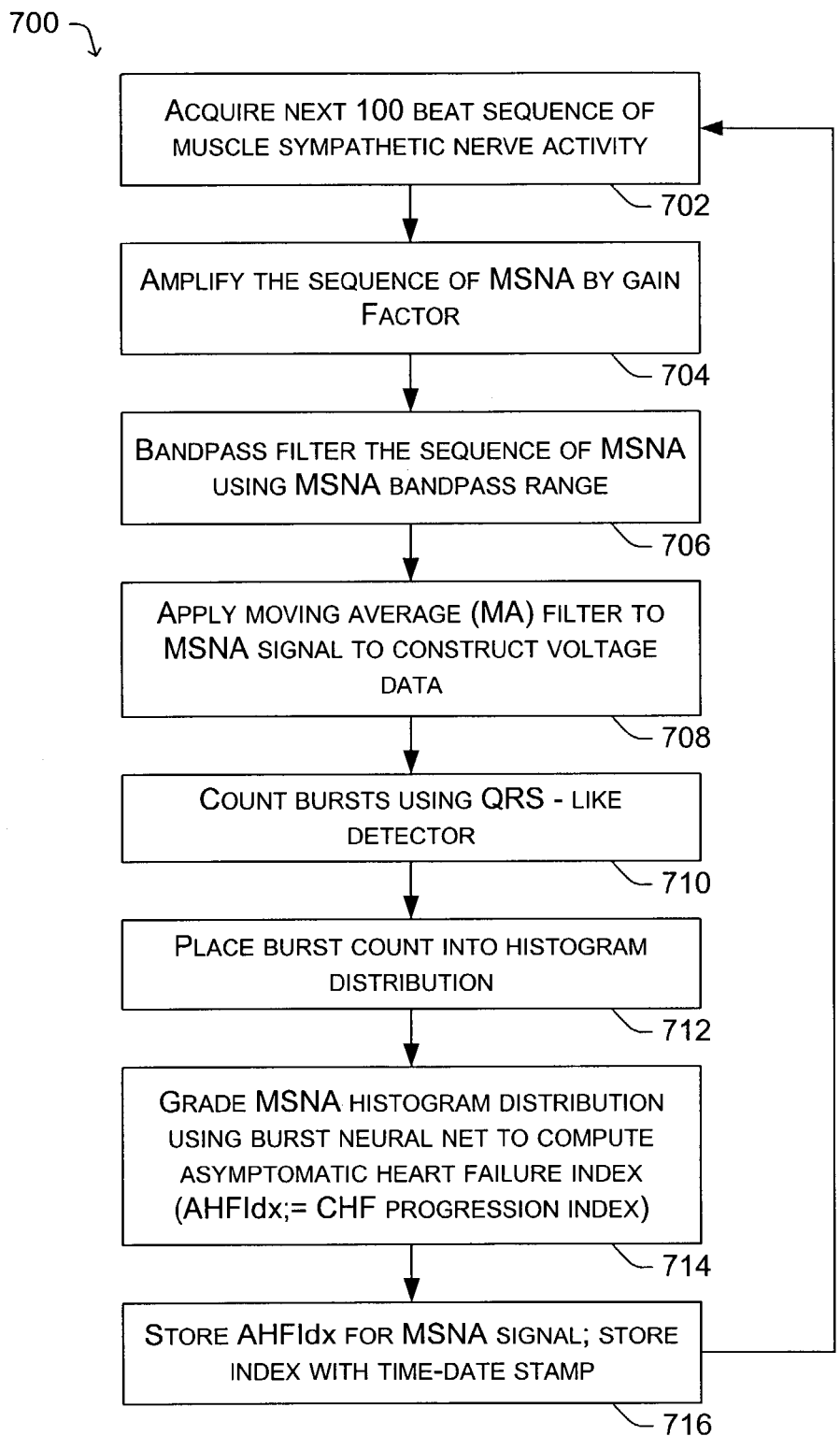
FIG. 7 is a flow-diagram depicting an additional method for use in determining heart failure, in accordance with certain exemplary implementations of the present invention.
Figure 8:
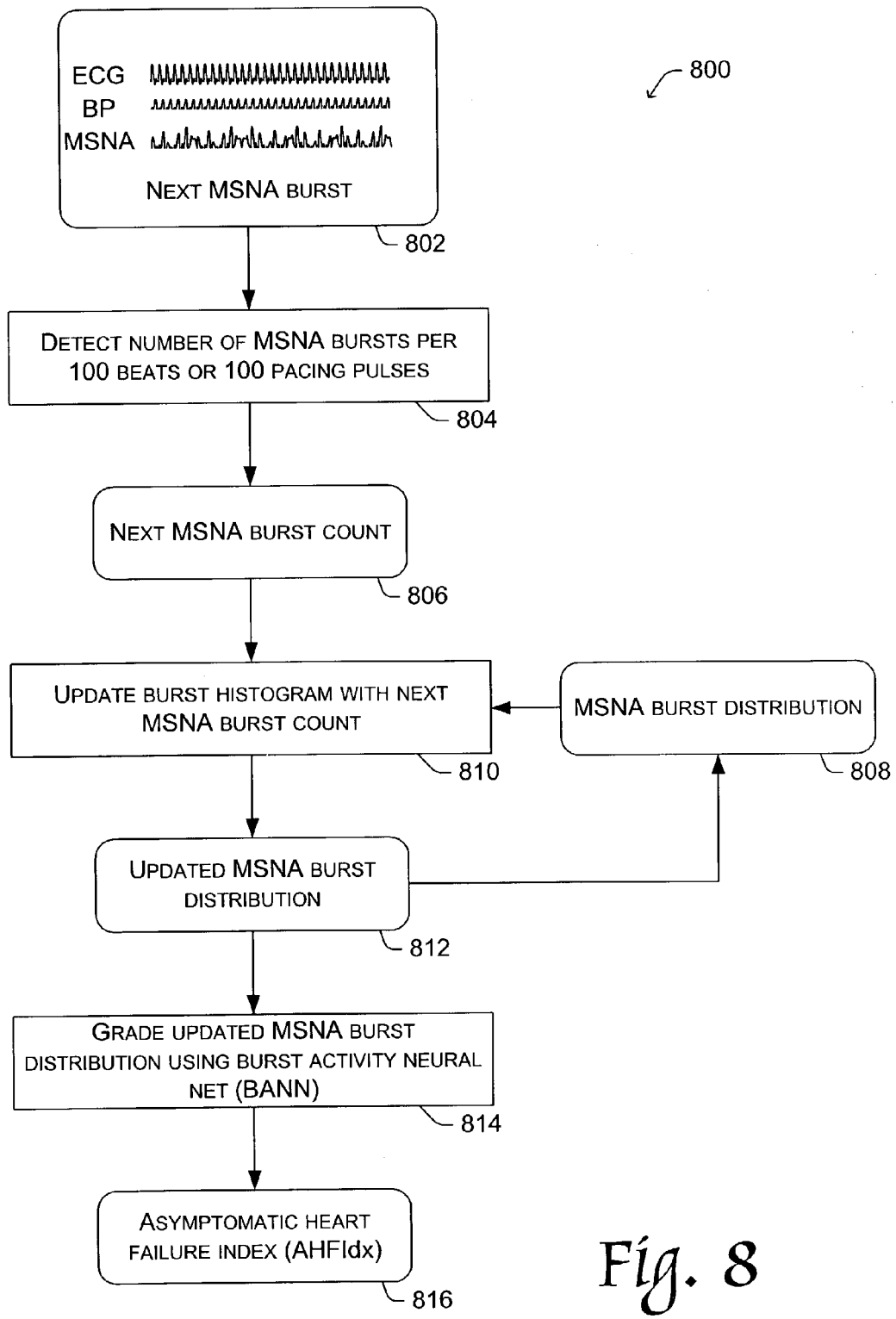
FIG. 8 is also a flow-diagram depicting a method for use in determining heart failure, in accordance with still other exemplary implementations of the present invention.
Figure 10:
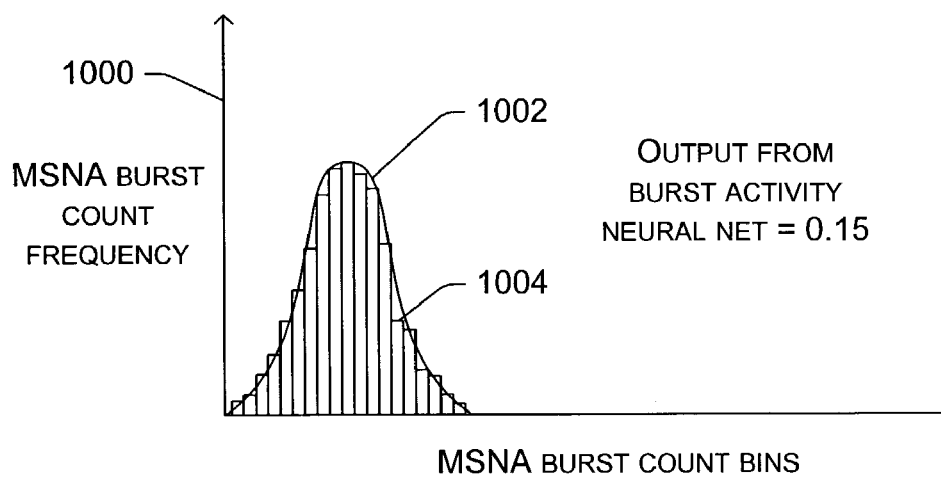
FIG. 10 depicts three graphs showing different histograms for detected MSNA bursts, in accordance with certain further exemplary implementations of the present invention.
Figure 10:
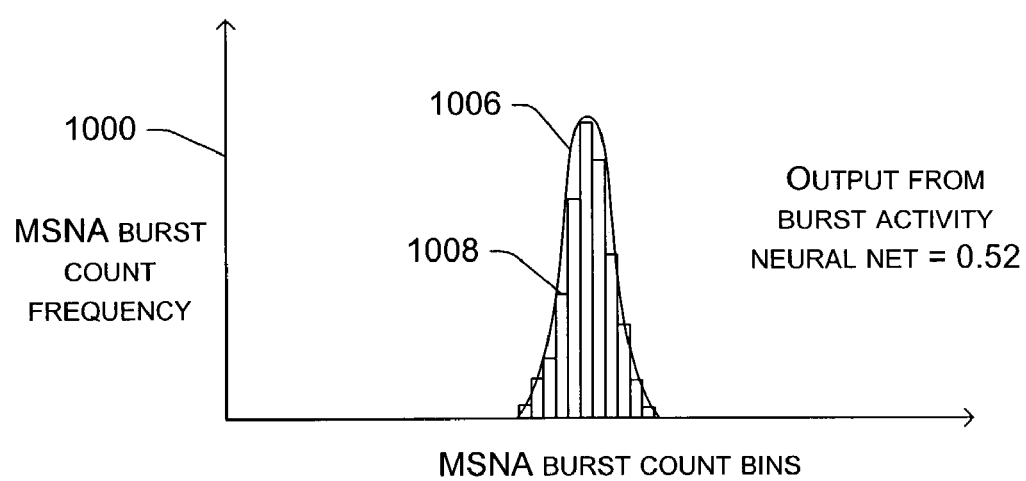
Figure 10:
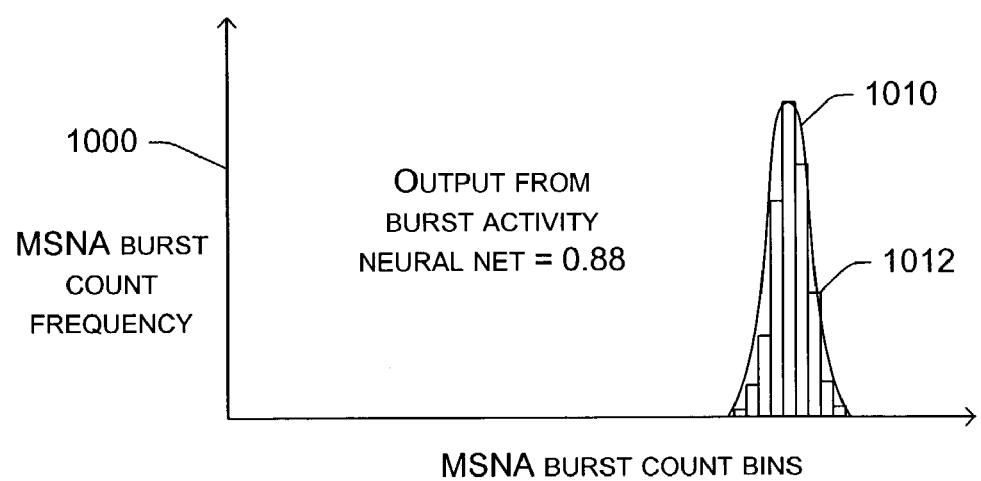

FIGS. 7, 8, and 10 illustrate methods associated with nerve activity acquisition and analysis logic, for example, as represented by act 402 in FIG. 4.

FIG. 7 illustrates a method 700 for computing an AHFIdx from a MSNA signal segment. An analog MSNA signal segment is acquired in act 702 using an ICD's physiological sensor hardware. In act 704, the MSNA signal data are amplified, e.g., by a value in the range between about 10,000, and about 100,000, as applicable. In act 706, the resulting amplified MSNA signal is then bandpass filtered based on an MSNA Bandpass Range. By way of example, in certain implementations the MSNA Bandpass Range is between about 500 Hz and about 2500 Hz. In act 708, the resulting bandpass filtered MSNA signal is then digitized using an A/D converter and passed through an integrating process, such as, e.g., a Moving Average (MA) filter. In certain exemplary implementations act 708 employs an MA(100) to an MA(500) filter with all weights equal, to implement an analog integration function with a time constant in the range of between about 0.01 seconds and about 0.25 seconds.

Other bandpass filtering methods to filter the MSNA signal are well-known and may be employed by those skilled in the art. Other such methods include, for example, autoregressive (AR) filtering, a combination of moving average and autoregressive (ARMA) filtering, linear prediction, etc. The filtering methods may be implemented using time domain techniques or frequency domain techniques. The filtering methods may be implemented with analog or digital hardware integrated with the ICD and with software subroutines, logic, etc., that a part of the AHFD.

In act 710, the MSNA signal data bursts are counted, for example, using an algorithm much like the many QRS detector algorithms that are developed and available. In act 712, the burst count for the MSNA signal data is placed into the proper bin of the burst count histogram.

The histogram distribution is input to a neural net, for example, in act 714, to compute an AHFIdx. The neural net is a feed-forward neural net taking a MSNA burst activity histogram as input and using its computational structure to construct the AHFIdx. Here, the neural net grades the MSNA burst activity histogram from 0 to 1, where a 0 means that the MSNA burst activity histogram indicates a patient without any significant trace of heart failure, and where a 1 means the MSNA burst activity histogram indicates a patient with severe heart failure.

In act 716, the resulting AHFIdx is stored along with other applicable data, such as, a time stamp.

FIG. 8 is a flow diagram depicting a process 800 in which MSNA signals are used to compute an AHFIdx. A patient's ECG, blood pressure (BP), and MSNA are shown in illustration 802. Here, the processed MSNA burst sequence is shown in reference to the patient's ECG and blood pressure. In act 804, the MSNA signal is monitored and sequences of MSNA burst data collected after a certain number of beats. For example, MSNA burst data may be collected every 100 beats and/or 100 pacing pulses to produce a corresponding next MSNA burst count 806. In act 810, next burst count 806 is combined with the MSNA burst histogram distribution 808 to construct an updated burst histogram distribution 812 using the new burst count value. Updated MSNA burst histogram distribution 812 is graded in act 814 using a burst activity neural net (BANN) or other like logical mechanism. The output from act 814 in this example is a number between 0 and 1, which is defined to be the AHFIdx 816.

FIG. 10 includes three graphs 1000 that illustrate various MSNA burst count bins along the x-axis and the MSNA burst count frequency along the y-axis. The upper graph illustrates a MSNA burst activity histogram 1004 and a corresponding smoothed approximating distribution 1002. Here, for example, MSNA burst activity histogram 1004 has been input to a BANN producing an output of about 0.15, indicating that the histogram represents MSNA signal data for a patient that probably does not have an asymptomatic heart failure condition.

The center graph illustrates a MSNA burst activity histogram 1008 and a corresponding smoothed approximating distribution 1006. Here, MSNA burst activity histogram 1008 has been input to a BANN producing an output of about 0.52. Here, MSNA burst activity histogram 1008 includes MSNA signal data indicating that a patient may have a medium level of severity of a heart failure condition.

The lower graph illustrates a MSNA burst activity histogram 1012 and a corresponding smoothed approximating distribution 1010. Exemplary MSNA burst activity histogram 1012 has been input to a BANN producing an output of about 0.88. As such, the histogram represents MSNA signal data indicative of a patient that probably has a severe level of a heart failure condition.

FIG. 9 illustrates the movement and changes of the burst activity histogram as a patients severity of heart failure progresses from none to severe, with a patient diagnosed with heart failure at some point between mild and severe. The progression from no heart failure to severe heart failure is gradual. The histogram remains unimodal, slowly shifting to the right as the disease progresses.

Figure 11:
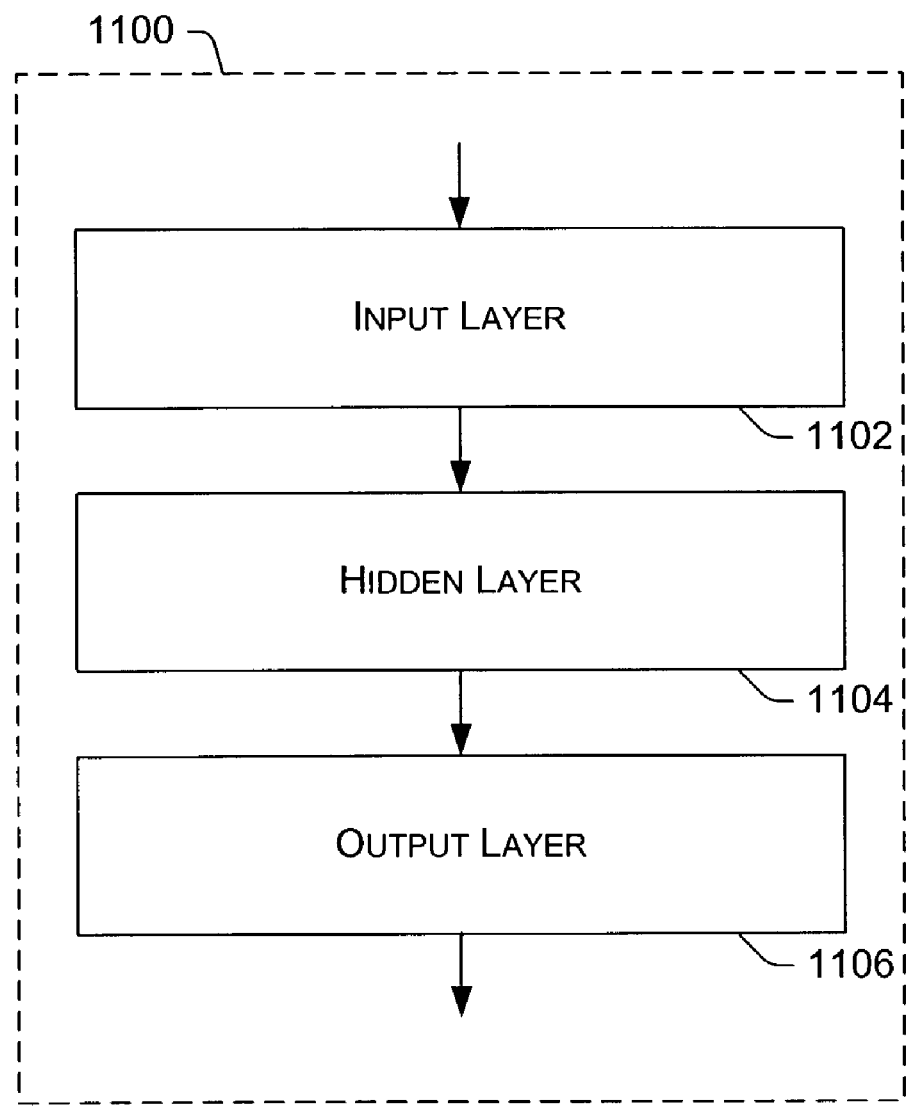
FIG. 11 is a block diagram depicting a representation of a three-layer network suitable for use in detecting heart failure, in accordance with certain further exemplary implementations of the present invention.

As illustrated in the block diagram in FIG. 11, in accordance with certain implementations of the present invention, a BANN may include a three-layer network 1100 having an input layer 1102, a hidden layer 1104, and an output layer 1106. Input layer 1102 feeds the burst activity histogram bin data to hidden layer 1104, in this example, without any weighting or nonlinear processing. Input layer 1102 has as many nodes as the number of bins for the burst activity histogram. Hidden layer 1104 computes a number of logistic (e.g., sigmoid) outputs from linear combinations of the histogram data, and passes these transformed data to output layer 1106. By way of example, in certain implementations, hidden layer 1104 includes between about four and eight nodes.

In this example, output layer 1106 is configured as a logistic classifier, using the outputs from hidden layer 1104 to compute a logistic (e.g., sigmoid) value from a weighted linear combination of the outputs from hidden layer 1104. In certain examples, output layer 1106 has one node configured to output a value from 0 to 1.

Neural net 1100 can be trained, for example, using a large data set of burst activity histograms constructed from four groups of patients, all of whom have a form of significant left ventricular impairment. The four groups of patients are (1) patents without any clinical or MSNA signs of heart failure, (2) patients with mild clinical symptoms, (3) patents with medium clinical symptoms, and (4) patients with severe clinical symptoms.

One reason for using a neural net to characterize a patient's burst activity histogram is the well-known and well-appreciated ability of a feed-forward neural net to capture the unique characteristics of each patient population's burst activity histogram and its ability to normalize its output through a training process to automatically provide an accurate linear severity scale when presented with a previously unknown burst activity histogram.

In certain implementations, an AHFD implements a neural net in software using the weights and parameters determined during the training process with the patient population's burst activity histograms. Methods for training a feed-forward neural net are well known. The most prominent method is the method of back-propagation. Much research and concise reference books on neural nets have become available since Rumelhart and McClelland first popularized the back-propagation method for training multilayer neural nets. A recent example of a patent for the training of a feed-forward neural net is U.S. Pat. No. 6,269,351.

An alternative implementation to using software codes to count the sympathetic nerve activity is to implement the processes described above using hardware and/or firmware that is configured to output a burst count. For example, a hardware/firmware peak detector for an electrogram signal in a pacemaker or defibrillator may be configured to detect bursts in a MSNA signal after the signal has been bandpass filtered and integrated (e.g., to provide a moving average function). Therefore, steps 702 through 710 can be implemented in hardware/firmware, providing fast and accurate burst counts for a MSNA signal continuously. Such an implementation may, for example, store a burst count continuously for the histogram placement software subsystem of the AHFD.

In still other exemplary implementations, rather that using a burst count histogram or neural net to classify a level of severity for asymptomatic heart failure, the neural net may be replaced with any statistical or other like method that characterizes the burst activity histogram or burst activity data set. For methods using burst counts, a first example is the value for the mean number of burst counts and a second example is the value for the standard deviation of the burst counts. Certain implementations may use median amplitude bursts, such as, for example, the value for the mean of the set of median amplitude burst values and/or the value for the standard deviation of the set of median amplitude burst values.

The above methods and apparatuses may provide for additional patient monitoring/treatment. For example, there are other types of disorders that have higher burst activity than normal, such as pituitary deficiency. Also, MSNA burst activity tends to naturally increase as patients get older without any disorders. Thus, a method of discriminating between the burst activity for heart failure and the MSNA burst activity for other such disorders and age may be implemented. One may also investigate whether patients with severe heart failure and after receiving a new heart through heart transplantation would continue to have high MSNA burst activity. Another method may be implemented to measure MSNA burst activity different from counting bursts, called the sympathetic neural burst amplitude distribution. For example, it has been determined that the burst amplitude indicator of sympathoexcitation in human heart failure is insensitive to age (e.g., burst frequency correlates with age but the median burst amplitude did not correlate with age; the median burst amplitude indicator remained constant throughout the age range), returns to normal in a patient with a heart transplant, and does not have increased levels for patients without heart failure.

The median burst amplitude may be computed using a MSNA signal segment. The amplitude of the largest (e.g., maximal) burst that occurred during the segment time period can be set to 100% and other burst amplitudes expressed as a percentage of the maximal burst. The burst amplitude percentage values can be used to construct a burst amplitude distribution. A median burst amplitude can be extracted as a sympathoexcitation indicator. The median burst amplitude would be the value at which 50% of the burst amplitudes are larger and 50% are smaller.

The median burst amplitude value can be used as a replacement value for the burst activity count described in the examples above. Using the median burst amplitude, the AHFD can monitor for the onset or progression of a patient's heart failure condition. Using the median burst amplitude, the AHFD will likely be insensitive to increases in MSNA due to age and due to other non-cardiac related disorders.

Those skilled in the art will recognize that any such derivable indicator of heart failure onset or progression from the MSNA can be substituted for burst count or median burst amplitude.

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for use with an implantable device, the method comprising:
   extracting muscle sympathetic nerve activity over a period of time from a sensed implantable electrode signal; and determining a level of heart failure based on the extracted muscle sympathetic nerve activity;

wherein the muscle sympathetic nerve activity is extracted by amplifying the sensed implantable electrode signal in the range between about 10,000 and about 100,000 and bandpass filtering the amplified activity signal on a musde sympathetic nerve activity bandpass range.

2. The method as recited in claim 1, further comprising: selectively applying cardiac stimulation therapy using at least one implantable cardiac stimulation electrode based at least in part on the determined level of heart failure.

3. The method as recited in claim 1, further comprising: outputting information to a non-implantable device based on the determined level of heart failure.

4. The method as recited in claim 1, wherein the sensed implantable electrode signal is sensed by at least one implantable electrode operatively configured on a lead.

5. The method as recited in claim 1, wherein the sensed implantable electrode signal is sensed by at least one implantable electrode operatively provided by at least a portion of a body of the implantable device.

6. The method as recited in claim 1, wherein muscle sympathetic nerve activity bandpass range is between about 500 Hz and about 2500 Hz.

7. An implantable device comprising:

a housing;

at least one implantable electrode that is operative to detect nerve activity;

circuitry, at least partially arranged within the housing, and configured to sense nerve activity over a period of time using the at least one implantable electrode and extract muscle sympathetic nerve activity from the nerve activity; and control circuitry operatively coupled to the circuitry and configured to determine a level of heart failure based on the extracted muscle sympathetic nerve activity;

wherein the circuitry is configured to extract a muscle sympathetic nerve activity signal by amplifying a nerve activity signal in the range between about 10,000 and about 100,000 and bandpass filtering the amplified nerve activity signal on a nerve activity bandpass range.

8. The implantable device as recited in claim 7, further comprising:

therapy applying circuitry, at least partially arranged within the housing and operatively coupled to the control circuitry and configurable to selectively apply shock therapy to a patient's heart based at least in part on the determined level of heart failure.

9. The implantable device as recited in claim 7, further comprising:

communication circuitry, at least partially arranged within the housing and operatively coupled to the control circuitry and configurable to output information to a non-implantable device based on the determined level of heart failure.

10. The implantable device as recited in claim 7, wherein the at least one implantable electrode is operatively configured on a lead that extends outwardly from the housing.

11. The implantable device as recited in claim 7, wherein at least a portion of the housing is configurable to act as the at least one implantable electrode.

12. The apparatus as recited in claim 7, wherein the nerve activity bandpass range is between about 500 Hz and about 2500 Hz.

13. A method for detecting heart failure, the method comprising:

sensing nerve activity using at least one nerve sensing electrode that is in electrical contact with a patient's efferent muscle-nerve structure, and extracting a corresponding muscle sympathetic nerve activity signal;

analyzing the muscle sympathetic nerve activity signal for changes in nerve burst activity over time; and determining a degree of heart failure based on the changes in nerve burst activity over time;

wherein the muscle sympathetic nerve activity signal is extracted by receiving a nerve activity signal from the at least one nerve sensing electrode, amplifying the nerve activity signal in the range between about 10,000 and about 100,000, and bandpass filtering the amplified nerve activity signal on a nerve activity bandpass range.

14. The method as recited in claim 13, wherein analyzing the nerve activity signal for changes in nerve burst activity further comprises:

producing a nerve burst count based on a number of applicable bursts in the nerve activity signal;

constructing histogram information based on the nerve burst count; and determining a degree of heart failure severity based on the histogram information.

15. The method as recited in claim 14, wherein determining the degree of heart failure further comprises using neural network logic to determine the degree of heart failure severity.

16. The method as recited in claim 14, wherein determining the degree of heart failure severity further comprises using at least one statistically derived histogram characteristic to determine the degree of heart failure severity.

17. The method as recited in claim 14, wherein the degree of heart failure severity is between 0 and 1.

18. The method as recited in claim 13, further comprising monitoring the degree of heart failure severity over an extended period of time to possibly detect long-term changes thereto.

19. The method as recited in claim 18, wherein monitoring the degree of heart failure severity over an extended period of time further comprises using linear regression analysis to detect the long-term changes.

20. The method as recited in claim 18, further comprising reporting the detected long-term changes.

21. The method as recited in claim 13, further comprising reporting information associated with the nerve burst activity and indicative of heart failure.

22. The method as recited in claim 21, wherein the information comprises degree of heart failure severity information.

23. The method as recited in claim 13, wherein sensing nerve activity is performed substantially continuously.

24. The method as recited in claim 13, wherein sensing nerve activity is performed periodically.

25. The method as recited in claim 13, wherein the efferent muscle-nerve structure comprises a pectoral structure.

26. The method as recited in claim 13, further comprising selectively applying shock therapy to the patients heart based on the nerve burst activity.

27. The method as recited in claim 13, wherein nerve activity bandpass range is between about 500 Hz and about 2500 Hz.

28. An apparatus for detecting heart failure in a patient, the apparatus comprising:

a nerve activity sensor operatively configurable to sense nerve activity within a patient and output a corresponding nerve activity signal; and control circuitry operatively coupled to the nerve activity sensor and configured to extract a muscle sympathetic nerve activity signal from the nerve activity signal and analyze the muscle sympathetic nerve activity signal for changes in nerve burst activity that is indicative of heart failure;

wherein the control circuitry is configured to extract the muscle sympathetic nerve activity signal by amplifying the nerve activity signal in the range between about 10,000 and about 100,000 and bandpass filtering the amplified nerve activity signal on a nerve activity bandpass range.

29. The apparatus as recited in claim 28, wherein the nerve activity sensor comprises at least one nerve sensing electrode configurable to be placed in electrical contact with a selected nerve fiber bundle within the patient.

30. The apparatus as recited in claim 29, wherein the selected nerve fiber bundle is within an efferent muscle-nerve structure that comprises a pectoral structure.

31. The apparatus as recited in claim 28, wherein the control circuitry is configured to analyze the muscle sympathetic nerve activity signal for changes in nerve burst activity by producing a nerve burst count based on a number of applicable bursts in the muscle sympathetic nerve activity signal, generating histogram information based on the nerve burst count, and determining a degree of heart failure severity based on the histogram information.

32. The apparatus as recited in claim 31, wherein the control circuitry further comprises neural network circuitry configured to determine the degree of heart failure severity.

33. The apparatus as recited in claim 31, wherein the control circuitry determines the degree of heart failure severity based on at least one statistically derived histogram characteristic.

34. The apparatus as recited in claim 28, further comprising:

treatment circuitry operatively coupled to the control circuitry and configured to selectively cause shock therapy to be applied to the patient's heart based on the nerve burst activity.

35. The apparatus as recited in claim 28, wherein the nerve activity bandpass range is between about 500 Hz and about 2500 Hz.

* * * * *